United States Patent
Ferrigno et al.

(10) Patent No.: US 7,799,825 B2
(45) Date of Patent: Sep. 21, 2010

(54) THIOPHENE AND THIAZOLE SUBSTITUTED TRIFLUOROETHANONE DERIVATIVES AS HISTONE DEACETYLASE (HDAC) INHIBITORS

(75) Inventors: Federica Ferrigno, Pomezia (IT); Philip Jones, Pomezia (IT); Ester Muraglia, Pomezia (IT); Jesus Maria Ontoria Ontoria, Pomezia (IT); Rita Scarpelli, Rome (IT); Carsten Schultz-Fademrecht, Pomezia (IT)

(73) Assignee: Istituto di Ricerche di Biologia Molecolare P. Angeletti SpA, Rome (IT)

( * ) Notice: Subject to any disclaimer, the term of this patent is extended or adjusted under 35 U.S.C. 154(b) by 0 days.

(21) Appl. No.: 12/223,943

(22) PCT Filed: Feb. 14, 2007

(86) PCT No.: PCT/GB2007/050061
§ 371 (c)(1),
(2), (4) Date: Aug. 13, 2008

(87) PCT Pub. No.: WO2007/093827
PCT Pub. Date: Aug. 23, 2007

(65) Prior Publication Data
US 2009/0076101 A1    Mar. 19, 2009

(30) Foreign Application Priority Data
Feb. 15, 2006  (GB) .................. 0603041.5

(51) Int. Cl.
*A61K 31/381*  (2006.01)
*C07D 333/04*  (2006.01)
(52) U.S. Cl. ....................... 514/448; 549/73
(58) Field of Classification Search ............... 514/365, 514/448; 549/73; 548/200
See application file for complete search history.

(56) References Cited

U.S. PATENT DOCUMENTS

| | | | |
|---|---|---|---|
| 7,425,643 B1 * | 9/2008 | Jen et al. | ................... 549/474 |
| 2003/0013757 A1 | 1/2003 | Leser-Reiff et al. | |
| 2004/0122079 A1 | 6/2004 | Grossmann et al. | |

FOREIGN PATENT DOCUMENTS

| | | |
|---|---|---|
| WO | WO88/00467 | 1/1988 |
| WO | WO91/19708 | 12/1991 |
| WO | WO02/46129 | 6/2002 |
| WO | WO03/011851 | 2/2003 |
| WO | WO03/099760 | 12/2003 |
| WO | WO2004/013130 | 2/2004 |
| WO | WO2004/054999 | 7/2004 |
| WO | WO2005/014588 | 2/2005 |
| WO | WO2005/034880 | 4/2005 |
| WO | WO2005/040161 | 5/2005 |
| WO | WO2005/086898 | 9/2005 |
| WO | WO2005/121120 | 12/2005 |
| WO | WO2005/121134 | 12/2005 |
| WO | WO2007/029035 | 3/2007 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*

* cited by examiner

*Primary Examiner*—Kamal A Saeed
*Assistant Examiner*—Kristin Bianchi
(74) *Attorney, Agent, or Firm*—Li Su; David A. Muthard

(57) ABSTRACT

The present invention relates to compounds of formula (I), and pharmaceutically acceptable salts and tautomers thereof. Compounds of the present invention are inhibitors of histone deacetylase (HDAC) and are useful for treating cellular proliferative diseases, including cancer. They are also useful for treating neurodegenerative diseases, mental retardation, 10 schizophrenia, inflammatory diseases, restenosis, immune disorders, diabetes, cardiovascular disorders and asthma.

(I)

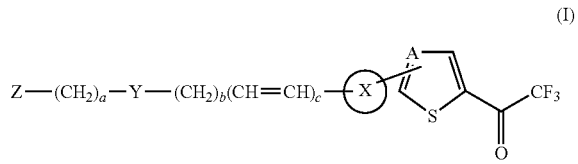

10 Claims, No Drawings

THIOPHENE AND THIAZOLE SUBSTITUTED
TRIFLUOROETHANONE DERIVATIVES AS
HISTONE DEACETYLASE (HDAC)
INHIBITORS

PRIORITY CLAIM

This application is a §371 National Stage Application of PCT/GB2007/050061, filed on Feb. 14, 2007, which claims priority from GB Provisional Application Serial Number 0603041.5, filed on Feb. 15, 2006.

BACKGROUND OF THE INVENTION

In eukaryotic cells the orderly packaging of DNA in the nucleus plays an important role in the regulation of gene transcription. Nuclear DNA is ordered in a compact complex called chromatin. The core of the complex is an octamer of highly conserved basic proteins called histones. Two each of histones H2A, H2B, H3 and H4 associate and DNA winds around the basic amino acids of the histones interacting with the negatively charged phosphate groups of the DNA. One molecule of histone H1 is associated with each wound core which accommodates approximately 146 hp of DNA. The cores are, in turn, packaged into a compact regular structure with about 200 bp of DNA between each core.

The amino-terminal tails of the histones are subject to post-translational modification, in particular by acetylation of lysine. Histone deacetylases (HDACs) and histone acetyl transferases (HATs) determine the pattern of histone acetylation, which together with other dynamic sequential post-translational modifications might represent a 'code' that can be recognised by non-histone proteins forming complexes involved in the regulation of gene expression. This and the ability of histone deacetylases (HDACs) to also modify non-histonic substrates and participate in multi-protein complexes contributes to the regulation of gene transcription, cell cycle progression and differentiation, genome stability and stress responses.

Eleven members of the HDAC family have been identified in humans, which share a conserved catalytic domain and are grouped into two classes: class I (1, 2, 3, 8), homologous to yeast Rpd3; class IIa (4, 5, 7, 9) and IIb (6, 10), homologous to yeast Hdal. HDAC11 shares homologies with both classes, but is at the same time distinct from all the other ten subtypes. Interest in these enzymes is growing because HDAC inhibitors (HDACi) are promising therapeutic agents against cancer and other diseases. The first generation of HDACi were discovered from cell-based functional assays and only later identified as HDAC class I/II inhibitors. Present HDAC inhibitors are pan-specific or poorly selective. Those that entered clinical trials all show similar adverse effects, mainly fatigue, anorexia, hematologic and GI-toxicity, that becomes dose-limiting in clinical trials. It is not at all clear whether the antitumor properties of HDAC inhibitors are due to their lack of specificity or are the consequence of hitting one or few "crucial" subtypes. This question is of considerable interest because it may open the way for the development of novel, more sensitive compounds with possibly enhanced efficacy and/or tolerability. More recent studies were therefore directed to better define the biological function of different class members and to devise subtype-selective enzymatic assays to assist in the development of improved cancer chemotherapies.

The class IIa HDACs contain a highly conserved C-terminal catalytic domain (~420 amino acids) homologous to yBDA1 and an N-terminal domain with no similarity to other proteins. The activity of the class IIa HDACs is regulated at several levels, including tissue-specific gene expression, recruitment of distinct cofactors and nucleocytoplasmic shuttling. Whereas most class I HDACs are ubiquitously expressed, class IIa HDACs are expressed in a restricted number of cell types.

HDAC inhibitors cause the induction of differentiation, growth arrest and/or apoptosis in a broad spectrum of transformed cells in culture and tumours in animals, including both haematological cancers and solid tumours. These inhibitory effects are believed to be caused, in part, by accumulation of acetylated proteins, such as nucleosomal histones, which appear to play a major role in regulation of gene transcription. A proposed mechanism for the anti-tumour effects of HDAC inhibitors is that the accumulation of acetylated histones leads to activation (and repression) of the transcription of a select number of genes whose expression causes inhibition of tumour cell growth. Expression profiling of cells cultured with HDAC inhibitors supports this model, as studies demonstrate that the expression of a small number of genes (2-5% of the expressed genes) is altered (activated or repressed). The mechanism of gene repression or activation is not well understood and might result from either direct or indirect effects of histone acetylation or from the increase in acetylation of proteins other than histones (e.g. transcription factors).

SUMMARY OF INVENTION

There is still much to be understood about the family of HDACs, including the varying functions of different HDACs and the range of HDAC substrates. The development of selective HDAC inhibitors might be important in defining their biological role and potential as therapeutic agents. Clinically, the optimal dose, timing and duration of therapy, as well as the most appropriate agents to combine with HDAC inhibitors, are still to be defined.

The compounds of this invention are useful in the inhibition of histone deacetylase, particularly class II histone deacetylase.

In particular, the compounds are HDAC 4, 5, 6 and 7 inhibitors and may additionally be active against other HDAC subtypes such as HDAC 1, 2, 3 and 8.

The present invention provides a compound of formula I:

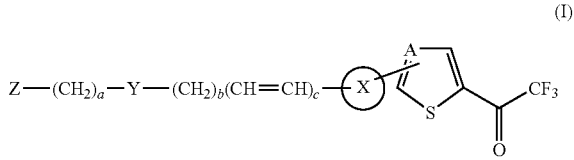

(I)

wherein:
a is 0, 1, 2 or 3;
b is 0, 1, 2 or 3;
c is 0, 1 or 2;
A is CH or N;
the X ring is a substituent on a carbon atom of the sulfur containing ring, and is $C_{6-10}$aryl, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms, or a 7-15 membered saturated, partially saturated or unsaturated heterocyclic ring containing 1, 2, 3 or 4 heteroatoms independently selected from N, O and S; optionally substituted by one or more halogen groups;

Y is a direct bond, 4, >(C=O), >S(O)$_d$, —NR$^2$(C=O)— or —(C=O)NR$^2$—;

d is 0, 1 or 2;

R$^2$ is hydrogen or C$_{1-6}$alkyl;

Z is hydrogen, halogen, cyano, hydroxyl, C$_{1-6}$alkyl, haloC$_{1-6}$alkyl, C$_{1-6}$alkoxy, nitro, N(R$^a$)$_2$; or a ring which is: C$_{3-4}$cycloalkyl; C$_{6-10}$aryl; a 5 or 6 membered saturated or partially saturated heterocyclic ring containing 1, 2 or 3 heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered saturated, partially saturated or unsaturated heterocyclic ring containing 1, 2, 3 or 4 heteroatoms independently selected from N, O and S; any of which rings being optionally substituted by one or more groups independently selected from R$^3$;

each R$^a$ is independently hydrogen, C$_{1-6}$alkyl, C$_{1-6}$alkylcarbonyl or SO$_2$R$^b$;

R$^b$ is C$_{1-6}$alkyl, amino, C$_{1-6}$alkylamino or di(C$_{1-6}$alkyl)amino;

each R$^3$ is independently halogen, cyano, oxo, hydroxyl, C$_{1-6}$alkyl, haloC$_{1-6}$alkyl, C$_{1-6}$alkoxy, mercaptoC$_{1-6}$alkyl, haloC$_{1-6}$alkoxy, nitro, N(R$^a$)$_2$, SO$_2$R$^b$, OSO$_2$R$^b$, COR$^c$, C$_{1-6}$alkylSO$_2$R$^b$, R$^d$, C$_{1-6}$alkylR$^d$, C$_{1-6}$alkoxyR$^d$ or C$_{1-6}$alkoxySO$_2$R$^d$;

R$^c$ is hydrogen, C$_{1-6}$alkyl or C$_{1-6}$alkoxy;

R$^d$ is C$_{6-10}$aryl; a 5-membered heteroaromatic ring containing 1, 2, 3 or 4 heteroatoms independently selected from N, O and S, not more than one heteroatom of which is O or S, or a 6 membered heteroaromatic ring containing 1, 2 or 3 nitrogen atoms; any of which rings being optionally substituted by one or more groups independently selected from halogen, C$_{1-6}$alkyl, C$_{1-6}$alkoxy, mercaptoC$_{1-6}$alkyl, haloC$_{1-6}$alkyl, haloC$_{1-6}$alkoxy, amino, C$_{1-6}$alkylamino and di(C$_{1-6}$alkyl)amino;

or a pharmaceutically acceptable salt or tautomer thereof, for use in therapy.

The present invention also provides a pharmaceutical composition comprising a compound of formula I as defined above, or a pharmaceutically acceptable salt or tautomer thereof in association with a pharmaceutically acceptable carrier.

The present invention also provides novel compounds of formula I:

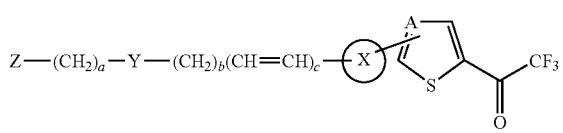

(I)

wherein:

a is 0, 1, 2 or 3;

b is 0, 1, 2 or 3;

c is 0, 1 or 2;

A is CH or N;

the X ring is a substituent on a carbon atom of the sulfur containing ring, and is C$_{6-10}$aryl, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms, or a 7-15 membered saturated, partially saturated or unsaturated heterocyclic ring containing 1, 2, 3 or 4 heteroatoms independently selected from N, O and S; optionally substituted by one or more halogen groups;

Y is a direct bond, —O—, >(C=O), >S(O)$_d$, —NR$^2$(C=O) or —(C=O)NR$^2$—;

d is 0, 1 or 2;

R$^2$ is hydrogen or C$_{1-6}$alkyl;

Z is hydrogen, halogen, cyano, hydroxyl, C$_{1-6}$alkyl, haloC$_{1-6}$alkyl, C$_{1-6}$alkoxy, nitro, N(R$^a$)$_2$; or a ring which is: C$_{3-6}$cycloalkyl; C$_{6-10}$aryl; a 5 or 6 membered saturated or partially saturated heterocyclic ring containing 1, 2 or 3 heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered saturated, partially saturated or unsaturated heterocyclic ring containing 1, 2, 3 or 4 heteroatoms independently selected from N, O and S; any of which rings being optionally substituted by one or more groups independently selected from R$^3$;

each R$^a$ is independently hydrogen, C$_{1-6}$alkyl, C$_{1-6}$alkylcarbonyl or SO$_2$R$^b$;

R$^b$ is C$_{1-6}$alkyl, amino, C$_{1-6}$alkylamino or di(C$_{1.6}$alkyl)amino;

each R$^3$ is independently halogen, cyano, oxo, hydroxyl, C$_{1-6}$alkyl, haloC$_{1-6}$alkyl, C$_{1-6}$alkoxy, mercaptoC$_{1-6}$alkyl, haloC$_{1-6}$alkoxy, nitro, N(R$^a$)$_2$, SO$_2$R$^b$, OSO$_2$R$^b$, COR$^c$, C$_{1-6}$alkylSO$_2$R$^b$, R$^d$, C$_{1-6}$alkylR$^d$, C$_{1-6}$alkoxyR$^d$ or C$_{1-6}$alkoxySO$_2$R$^d$;

R$^c$ is hydrogen, C$_{1-6}$alkyl or C$_{1-6}$alkoxy;

R$^d$ is C$_{6-10}$aryl; a 5-membered heteroaromatic ring containing 1, 2, 3 or 4 heteroatoms independently selected from N, O and S, not more than one heteroatom of which is O or S, or a 6 membered heteroaromatic ring containing 1, 2 or 3 nitrogen atoms; any of which rings being optionally substituted by one or more groups independently selected from halogen, C$_{1-6}$alkyl, C$_{1-6}$alkoxy, mercaptoC$_{1-6}$alkyl, haloC$_{1-6}$alkyl, haloC$_{1-6}$alkoxy, amino, C$_{1-6}$alkylamino and di(C$_{1-6}$alkyl)amino;

providing that:

when A is CH and X is phenyl, then (CH=CH)$_c$(CH$_2$)$_b$—Y—(CH$_2$)$_a$-Z is not hydrogen;

or pharmaceutically acceptable salts or tautomers thereof.

In one embodiment of the above embodiments, when A is N then (CH=CH)$_c$(CH$_2$)$_b$—Y—(CH$_2$)$_a$-Z is selected from hydrogen, halogen, haloC$_{1-6}$alkyl, cyano, nitro, C$_{1-6}$alkoxy, C$_{1-6}$alkylcarbonyl, C$_{6-10}$aryl or C$_{6-10}$aryloxy.

In another embodiment of the above embodiments, when A is N then (CH=CH)$_c$(CH$_2$)$_b$—Y—(CH$_2$)$_n$-Z is selected from hydrogen, halogen, cyano, nitro, C$_{1-6}$alkoxy, C$_{1-6}$aryl or C$_{6-10}$aryloxy.

For the avoidance of doubt, when A is substituted then A is C.

In an embodiment A is CH.

In another embodiment A is N.

Preferably a is 0, 1 or 2.

Preferably b is 0, 1 or 2. More particularly b is 0 or 1.

Preferably c is 0 or 1.

Particular X rings include phenyl, quinolinyl, triazolyl, oxadiazolyl, quinoxalinyl, pyridinyl, benzothienyl, thiazolyl, pyrazolyl, isoquinolinyl, pyrimidinyl, thianthrenyl, dihydrobenzofuranyl, benzodioxolyl, dihydrobenzodioxinyl, indolyl and naphthyl, optionally substituted by one or more halogen groups.

Preferably, X is unsubstituted or monosubstituted.

More specifically, the X rings as attached to the central sulfur containing ring include phenyl, quinolin-6-yl, 1,2,3-triazol-4-yl, 1,2,4-oxadiazol-5-yl, quinoxalin-6-yl, pyridin-3-yl, quinolin-8-yl, quinolin-3-yl, 1-benzothien-7-yl, 1,3- thiazol-2-yl, 1H-pyrazol-3-yl, isoquinolin-5-yl, pyrimidin-5-yl, 1-benzothien-3-yl, thianthren-1-yl, 2,3-dihydro-1-benzofuran-5-yl, 1,3-benzodioxol-5-yl, 1,3,4-oxadiazol-2-yl, pyridin-2-yl, 2,3-dihydro-1,4-benzodioxin-yl, 1H-indol-5-yl, pyridin-4-yl, 2-naphthyl and 1-naphthyl.

In an embodiment when A is N then X is substituted by one, two or three halogen groups. Preferably X is monosubstituted by halogen. Favoured halogen groups are chlorine and fluorine.

In another embodiment X is unsubstituted.

Preferably, $R^2$ is hydrogen or methyl.

In an embodiment Y is a direct bond.

Preferably, Z is hydrogen, cyano, hydroxy, $C_{1-4}$alkyl, halo$C_{1-4}$alkyl, $C_{1-4}$alkoxy, nitro, $N(R^a)_2$; or a ring which is: morpholinyl, phenyl, naphthyl, cyclohexyl, pyridinyl, pyrazinyl, thienyl, pyrrolidinyl, dihydrobenzodioxinyl, pyrazolyl, quinoxalinyl, benzothiazolyl, cyclobutyl, dihydrobenzoxazolyl, dihydrobenzoxazinyl, furyl, benzodioxolyl or piperidinyl; any of which rings being optionally substituted by one or more groups independently selected from $R^3$.

More particularly, Z is morpholinyl, methyl, hydroxy, dimethylamino, hydrogen, phenyl, naphthyl, cyclohexyl, pyridinyl, pyrazinyl, thienyl, pyrrolidinyl, isopropyl, dihydrobenzodioxinyl, methoxy, pyrazolyl, quinoxalinyl, nitro, trifluoromethyl, tert-butoxy, methylsulfonylamino, benzothiazolyl, cyclobutyl, dihydrobenzoxazolyl, dihydrobenzoxazinyl, furyl, benzodioxolyl, cyano or piperidinyl; any of which rings being optionally substituted by one or more groups independently selected from $R^3$.

Preferably, when Z is a ring it is optionally substituted by one, two or three groups independently selected from $R^3$. More particularly, the ring is unsubstituted, monosubstituted or disubstituted.

Particular $R^3$ groups are methyl, dimethylsulfamate, fluoro, trifluoromethyl, carboxaldehyde, butyl, chloro, cyano, methylsulfonyl, phenylsulfonylmethyl, ethoxy, dichlorophenylmethoxy, [chloro(trifluoromethyl)pyridinyl]methoxy, trifluoromethoxy, [(chlorophenyl)sulfonyl]methyl, oxo, phenylsulfonyl, (methylthiazolyl)methoxy, methoxy, (chlorophenyl)sulfonyl, acetylamino, oxadiazolyl and bromo.

Specific $R^3$ groups include methyl, dimethylsulfamate, fluoro, trifluoromethyl, carboxaldehyde, tert-butyl, chloro, cyano, methylsulfonyl, phenylsulfonylmethyl, ethoxy, 2,4-dichlorophenylmethoxy, [3-chloro-5-trifluoromethyl)pyridin-2-yl]methoxy, trifluoromethoxy, [(4-chlorophenyl)sulfonyl]methyl, oxo, phenylsulfonyl, (2-methyl-1,3-thiazol-4-yl)methoxy, methoxy, (4-chlorophenyl)sulfonyl, acetylamino, 1,3,4-oxadiazol-2-yl and bromo.

Thus particular Z groups are morpholinyl, methyl, hydroxy, dimethylamino, hydrogen, phenyl, naphthyl, cyclohexyl, methylpyridinyl, pyridinyl, dimethylsulfamatephenyl, fluorophenyl, pyrazinyl, thienyl, trifluoromethylpyridinyl, trifluoromethylphenyl, methylphenyl, pyrrolidinyl, carboxaldehydephenyl, iso-propyl, dihydrobenzodioxinyl, tert-butylphenyl, chlorophenyl, dichlorophenyl, methoxy, dimethylpyrazolyl, pyrazolyl, quinoxalinyl, nitro, trifluoromethyl, tert-butoxy, methylsulfonylamino, cyanophenyl, methylsulfonylphenyl, (phenylsulfonylmethyl)phenyl, benzothiazolyl, cyclobutyl, ethoxyphenyl, (dichlorophenylmethoxy)phenyl, {[(chloro)(trifluoromethyl)pyridinyl]methoxy}phenyl, bis(trifluoromethyl)phenyl, (chloro)(fluoro)phenyl, trifluoromethoxyphenyl, {[(4-chlorophenyl)sulfonyl]methyl}phenyl, (oxo)dihydrobenzoxazolonyl, (oxo)dihydrobenzoxazinonyl, (chloro)(phenylsulfonyl)dihydrobenzoxazinonyl, [(methylthiazolyl)methoxy]phenyl, difluorophenyl, methoxyphenyl, [(chlorophenyl))sulfonyl]dihydrobenzoxazinyl, acetylaminophenyl, oxadiazolylphenyl, (bromo)(methyl)pyrazolyl, (fluoro)(methylphenyl, furyl, benzodioxolyl, dimethoxyphenyl, cyano and piperidinyl.

Specific Z groups include morpholin-4-yl, methyl, hydroxy, dimethylamino, hydrogen, phenyl, 2-naphthyl, cyclohexyl, 3-methylpyridin-2-yl, pyridin-4-yl, pyridin-2-yl, 4-(dimethylsulfamatephenyl, 4-fluorophenyl, pyrazin-2-yl, 2-thienyl, 6-trifluoromethylpyridin-3-yl, 4-trifluoromethylphenyl, pyridin-3-yl, 4-methylphenyl, pyrrolidin-1-yl, 4-carboxaldehydephenyl, iso-propyl, 2,3-dihydro-1,4-benzodioxin-2-yl, 4-tert-butylphenyl, 4-chlorophenyl, 2,4-dichlorophenyl, 3,4-dichlorophenyl, methoxy, 3,5-dimethyl-1H-pyrazol-1-yl, 1H-pyrazol-1-yl, quinoxalin-6-yl, nitro, trifluoromethyl, tert-butoxy, methylsulfonylamino, 4-cyanophenyl, 4-methylsulfonylphenyl, 2-(phenylsulfonylmethyl)phenyl, 1,3-benzothiazol-2-yl, cyclobutyl, 2-ethoxyphenyl, 4-(2,4-dichlorophenylmethoxy)phenyl, 4-{[3-chloro-5-(trifluoromethyl)pyridin-2-yl]methoxy}phenyl, 3,5-bis(trifluoromethyl)phenyl, 2-chloro-4-fluorophenyl, 3-trifluoromethyl)phenyl, 4-trifluoromethoxy)phenyl, 3-{[(4-chlorophenyl)sulfonyl]methyl}phenyl, 2-oxo-2,3-dihydro-1,3-benzoxazol-3(3H)-onyl, 3-oxo-2,3-dihydro-1,4-benzoxazin-4(4H)-onyl, 6-chloro-4-(phenylsulfonyl)-3,4-dihydro-2H-1,4-benzoxazin-2-onyl, 4-[(2-methyl-1,3-thiazol-4-yl)methoxy]phenyl, 2,4-difluorophenyl, 4-methoxyphenyl, 4-[(4-chlorophenyl)sulfonyl]-3,4-dihydro-2H-1,4-benzoxazin-2-yl, 4-acetylaminophenyl, 4-(1,3,4-oxadiazol-2-yl)phenyl, 3-methylphenyl, 4-bromo-1-methyl-1H-pyrazol-3-yl, 3-fluoro-4-methylphenyl, 3-methoxyphenyl, 2-furyl, 1,3-benzodioxol-5-yl, 2,5-dimethoxyphenyl, 2-fluorophenyl, 2-chlorophenyl, cyano and piperidin-1-yl.

In an embodiment $(CH=CH)_c(CH_2)_b—Y—(CH_2)_a$-Z is not hydrogen.

In an embodiment Z is not hydrogen.

Preferably, each $R^a$ is independently hydrogen, methyl, acetyl or methylsulfonyl.

Preferably, $R^b$ is methyl or dimethylamino.

Preferably, $R^c$ is hydrogen.

Preferably, $R^d$ is phenyl, thiazolyl, oxadiazolyl or pyridinyl, optionally substituted by one or more groups independently selected from halogen, $C_{1-4}$alkyl or halo$C_{1-2}$alkyl.

Preferably $R^d$ is optionally substituted by one, two or three groups. More particularly, $R^d$ is unsubstituted, monosubstituted or disubstituted.

Thus, particular $R^d$ groups are phenyl, dichlorophenyl, (chloro)(trifluoromethyl)pyridinyl, chlorophenyl, methylthiazolyl and oxadiazolyl.

More specifically, $R^d$ is phenyl, 2,4-dichlorophenyl, 3-chloro)-5-trifluoromethyl)pyridin-2-yl, 2-methyl-1,3-thiazol-4-yl or 1,3,4-oxadiazol-2-yl.

The present invention also provides compounds of formula II:

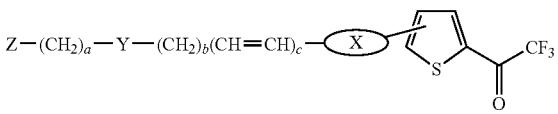

(II)

wherein a, b, c, X, Y and Z are as defined above;

provided that when X is phenyl, then $(CH=CH)_c(CH_2)_b—Y—(CH_2)_a$-Z is not hydrogen;

or a pharmaceutically acceptable salt or tautomer thereof.

The present invention also provides compounds of formula III:

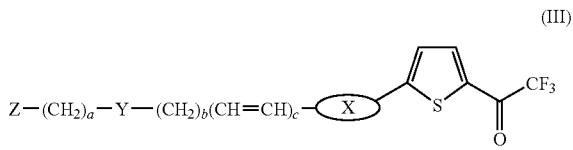

(III)

wherein a, b, c, X, Y and Z are as defined above;
provided that when X is phenyl, then $(CH=CH)_c(CH_2)_b-Y-(CH_2)_a-Z$ is not hydrogen;

or a pharmaceutically acceptable salt or tautomer thereof.

The present invention also provides compounds of formula IV:

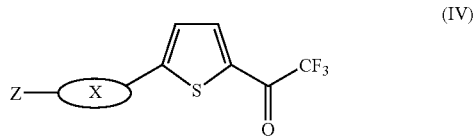

(IV)

wherein X and Z are as defined above;
provided that when X is phenyl, then Z is not hydrogen;

or a pharmaceutically acceptable salt or tautomer thereof.

The present invention also provides compounds of formula V:

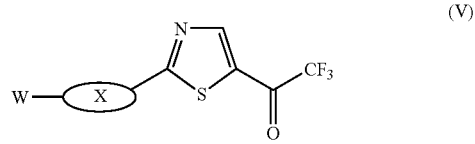

(V)

wherein:
X is $C_{6-10}$aryl, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms, or a 7-15 membered saturated, partially saturated or unsaturated heterocyclic ring containing 1, 2, 3 or 4 heteroatoms independently selected from N, O and S, optionally substituted by one or more halogen groups; and W is hydrogen, halogen, halo$C_{1-6}$alkyl, cyano, nitro, $C_{1-6}$alkoxy, $C_{1-6}$alkylcarbonyl, $C_{6-10}$aryl or $C_{6-10}$aryloxy;

or a pharmaceutically acceptable salt or tautomer thereof.

For the avoidance of doubt, the substituents on X can be substituted at any substitutable position.

The preferred identities with reference to formulae II, III, IV and V are as defined previously for formula I mutatis mutandis.

In an embodiment, W is hydrogen, halogen, cyano, nitro, $C_{1-6}$alkoxy, $C_{6-10}$aryl or $C_{6-10}$aryloxy.

In an embodiment X is phenyl, pyridinyl or naphthyl, optionally substituted by one halogen group.

In another embodiment the X ring as attached to the central thiazole ring is phenyl, pyridin-4-yl, 2-naphthyl or 1-naphthyl, optionally substituted by chlorine or fluorine.

Preferably, W is hydrogen, acetyl, cyano, phenoxy, phenyl, trifluoromethyl, nitro, chlorine, bromine or fluorine.

The present invention also includes within its scope N-oxides of the compounds of formula I above. In general, such N-oxides may be formed on any available nitrogen atom. The N-oxides may be formed by conventional means, such as reacting the compound of formula I with oxone in the presence of wet alumina.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula I and salts thereof, for example, hydrates.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention. In addition, the compounds disclosed herein may exist as tautomers and both tautomeric forms are intended to be encompassed by the scope of the invention, even though only one tautomeric structure is depicted.

The compounds may exist in different isomeric forms, all of which are encompassed by the present invention.

When any variable (e.g. $R^3$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents. A substituent on a saturated, partially saturated or unsaturated heterocycle can be attached at any substitutable position.

As used herein, "alkyl" is intended to include both branched and straight-chain saturated aliphatic hydrocarbon groups having the specified number of carbon atoms. For example, "$C_{1-6}$alkyl" is defined to include groups having 1, 2, 3, 4, 5 or 6 carbons in a linear or branched arrangement. For example, "$C_{1-6}$alkyl" specifically includes methyl, ethyl, n-propyl, i-propyl, n-butyl, t-butyl, i-butyl, pentyl, hexyl, and so on. Preferred alkyl groups are methyl and ethyl. The term "cycloalkyl" means a monocyclic, bicyclic or polycyclic saturated aliphatic hydrocarbon group having the specified number of carbon atoms. For example, "$C_{3-7}$cycloalkyl" includes cyclopropyl, methyl-cyclopropyl, 2,2-diethyl-cyclobutyl, 2-ethyl-cyclopentyl, cyclohexyl, and so on. In an embodiment of the invention the term "cycloalkyl" includes the groups described immediately above and further includes monocyclic unsaturated aliphatic hydrocarbon groups. For example, "cycloalkyl" as defined in this embodiment includes cyclopropyl, methyl-cyclopropyl, 2,2-dimethylcyclobutyl, 2-ethyl-cyclopentyl, cyclohexyl, cyclopentenyl, cyclobutenyl, 7,7-dimethylbicyclo[2.2.1]heptyl and so on. Preferred cycloalkyl groups are cyclopropyl, cyclobutyl, cyclopentyl and cyclohexyl.

As used herein, the term "$C_{2-6}$alkenyl" refers to a non-aromatic hydrocarbon radical, straight or branched, containing from 2 to 6 carbon atoms and at least one carbon to carbon double bond. Preferably one carbon to carbon double bond is present, and up to four non-aromatic carbon-carbon double bonds may be present. Alkenyl groups include ethenyl, propenyl, butenyl and 2-methylbutenyl. Preferred alkenyl groups include ethenyl and propenyl.

As used herein, the term "$C_{2-6}$alkenyl" refers to a hydrocarbon radical straight or branched, containing from 2 to 6 carbon atoms and at least one carbon to carbon triple bond. Up to three carbon-carbon triple bonds may be present. Alkynyl groups include ethynyl, propynyl, butynyl, 3-methylbutynyl and so on. Preferred alkynyl groups include ethynyl and propynyl.

"Alkoxy" represents an alkyl group of indicated number of carbon atoms attached through an oxygen bridge. "Alkoxy" therefore encompasses the definitions of alkyl above. Examples of suitable alkoxy groups include methoxy, ethoxy, n-propoxy, i-propoxy, n-butoxy, s-butoxy and t-butoxy. The preferred alkoxy groups are methoxy and ethoxy. The term '$C_{6-40}$aryloxy' can be construed analogously, and an example of this group is phenoxy.

As used herein, the term "mercapto$C_{1-6}$alkyl" represents a SH group attached through an alkyl group of indicated number. Examples of suitable mercaptoalkyl groups include $CH_2SH$, $CH_2CH_2SH$ and $CH_2CH_2CH_2SH$.

The terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular fluoro$C_{1-3}$alkyl and fluoro$C_{1-3}$alkoxy groups, for example, $CF_3$, $CHF_2$, $CH_2F$, $CH_2CH_2F$, $CH_2CHF_2$, $CH_2CF_3$, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

The term "$C_{1-6}$alkylcarbonyl" denotes a $C_{1-6}$alkyl radical, attached via a carbonyl (C=O) radical. Suitable examples of $C_{1-6}$alkylcarbonyl groups include methylcarbonyl, ethylcarbonyl, propylcarbonyl, isopropylcarbonyl and tert-butylcarbonyl.

The rings present in the compounds of this invention may be monocyclic or multicyclic, particularly bicyclic. The multicyclic rings may be fused or spiro linked.

As used herein, "$C_{6-10}$aryl" is intended to mean any stable monocyclic or bicyclic carbon ring of 6 to 10 atoms, wherein at least one ring is aromatic. Examples of such aryl elements include phenyl, naphthyl, tetrahydronaphthyl, indanyl and tetrahydrobenzo[7]annulene. The preferred aryl group is phenyl or naphthyl, especially phenyl.

Examples of particular heterocycles of this invention are benzimidazolyl, benzofurandionyl, benzofuranyl, benzofurazanyl, benzopyrazolyl, benzotriazolyl, benzothienyl, benzoxazolyl, benzoxazolonyl, benzothiazolyl, benzothiadiazolyl, benzodioxolyl, benzoxadiazolyl, benzoisoxazolyl, benzoisothiazolyl, chromenyl, chromanyl, isochromanyl, carbazolyl, carbolinyl, cinnolinyl, epoxidyl, furyl, furazanyl, imidazolyl, indolinyl, indolyl, indolizinyl, indolinyl, isoindolinyl, indazolyl, isobenzofuranyl, isoindolyl, isoquinolyl, isothiazolyl, isoxazolyl, naphthpyridinyl, oxadiazolyl, oxazolyl, oxazolinyl, isoxazolinyl, oxetanyl, purinyl, pyranyl, pyrazinyl, pyrazolyl, pyridazinyl, pyridopyridinyl, pyridazinyl, pyridinyl, pyrimidinyl, triazinyl, tetrazinyl, pyrrolyl, quinazolinyl, quinolinyl, quinoxalinyl, quinolizinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidyl, pyridin-2-onyl, pyrrolidinyl, imidazolinyl, imidazolidinyl, pyrazolinyl, pyrrolinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydroisoquinolinyl, dihydrotetrazolyl, dihydrothiadiazolyl, dihydrothiazolyl, dihydrothienyl, dihydrotriazolyl, dihydroazetidinyl, dihydroisochromenyl, dihydroimidazolonyl, dihydrotriazolonyl, dihydrobenzodioxinyl, dihydrothiazolopyrimidinyl, dihydroimidazopyrazinyl, methylenedioxybenzoyl, tetrahydrofuranyl, tetrahydrothienyl, tetrahydroquinolinyl, thiazolidinonyl, imidazolonyl, isoindolinonyl, octahydroquinolizinyl, octahydroisoindolyl, imidazopyridinyl, azabicycloheptanyl, chromenonyl, triazolopyrimidinyl, dihydrobenzoxazinyl, thiazolotriazolyl, azoniabicycloheptanyl, azoniabicyclooctanyl, phthalazinyl, naphthyridinyl, quinazolinyl, pteridinyl, dihydrobenzoxazinyl and thianthrenyl and N-oxides thereof. Further examples include thiazolotriazolyl, dihydrothiazolopyrimidinyl, dihydrobenzofuranyl, benzimidazolyl, benzofuranyl, dihydrobenzoxazolyl, dihydroquinazolinyl, dihydrophthalazinyl, indazolyl, benzisoxazolyl, tetrahydronaphthyridinyl, triazolopyrimidinyl, dibenzo[b,d] furanyl, naphthyridinyl, dihydroquinolinyl, dihydroisochromenyl, dihydrochromenyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, quinazolinyl, indolizinyl, azoniaspiro[5.5]undecanyl, azepanyl, octahydroindolizinyl, 1,2-dihydrospirocyclohexane-1,3-indolyl, octahydroisoindolyl, azoniabicyclo[3.1.0]hexanyl, diazoniaspiro[4.4]nonanyl, hexahydropyrrolo[3,4-b]pyrrolyl, oxaazoniabicyclo[2.2.1]heptanyl, diazoniaspriro[5.5]undecanyl, diazoniaspiro[3.3]heptanyl, diazoniaspiro[3.5]nonanyl, diazoniaspiro[4.5]decanyl, octahydropyrrolo[3,4-c]pyrrolyl, octahydropyrrolo[3,4-b]pyrrolyl, octahydrocyclopenta[c]pyrrolyl, dihydroindolyl, azoniaspiro[4.5]decanyl, diazoniabicyclo[2.2.2]octanyl, diazoniabicyclo[2.2.1]heptanyl, diazoniabicyclo[3.2.1]octanyl, diazoniabicyclo[2.2.1]heptanyl, azoniabicyclo[3.1.0]hexanyl, tetrahydrothiophenyl, oxaazoniaspiro[4.5]decanyl and oxazepanyl and N-oxides thereof. Attachment of a heterocyclyl substituent can occur via a carbon atom or via a heteroatom.

Preferred 5 or 6 membered saturated or partially saturated hetereocycles are pyrrolidinyl, piperidinyl, piperazinyl, morpholinyl and tetrahydrofuran.

Preferred 5 membered heteroaromatic rings are thienyl, thiazolyl, pyrazolyl, isoxazolyl, imidazolyl, thiadiazolyl, oxazolyl, oxadiazolyl, triazolyl, furyl and pyrrolyl.

Preferred 6 membered heteraromatic rings are pyridinyl, pyrazinyl and pyrimidinyl.

Preferred 7-15 membered saturated, partially saturated or unsaturated heterocyclic rings are tetrahydroquinolinyl, quinolinyl, indolyl, imidazopyridinyl, benzothiazolyl, quinoxalinyl, benzothiadiazolyl, benzoxazolyl, dihydrobenzodioxinyl, benzotriazolyl, benzodioxolyl, dihydroisoindolyl, dihydroindolyl, tetrahydroisoquinolinyl, isoquinolinyl, benzoisothiazolyl, dihydroimidazopyrazinyl, thianthrenyl, benzothienyl, dihydrobenzofuranyl, dihydrobenzoxazolyl and dihydrobenzoxazinyl. Further preferred rings include thiazolotriazolyl, dihydrothiazolopyrimidinyl, dihydrobenzofuranyl, benzimidazolyl, benzofuranyl, dihydrobenzoxazolyl, dihydroquinazolinyl, dihydrophthalazinyl, indazolyl, benzisoxazolyl, tetrahydronaphthyridinyl, triazolopyrimidinyl, dibenzo[b,d]furanyl, naphthyridinyl, dihydroquinolinyl, dihydroisochromenyl, dihydrochromenyl, dihydrobenzothiazolyl, imidazothiazolyl, tetrahydroindazolyl, tetrahydrobenzothienyl, hexahydronaphthyridinyl, tetrahydroimidazopyridinyl, tetrahydroimidazopyrazinyl, pyrrolopyridinyl, quinazolinyl, indolizinyl, azoniaspiro[5.5]undecanyl, azepanyl, octahydroindolizinyl, 12-dihydrospirocyclohexane-1,3-indolyl, octahydroisoindolyl, azoniabicyclo[3.1.0]hexanyl, diazoniaspiro[4.4]nonanyl, hexahydropyrrolo[3,4-b]pyrrolyl, oxaazoniabicyclo[2.2.1]heptanyl, diazoniaspriro[5.5]undecanyl, diazoniaspiro[3.3]heptanyl, diazoniaspiro[3.5]nonanyl, diazoniaspiro[4.5]decanyl, octahydropyrrolo[3,4-c]pyrrolyl, octahydropyrrolo[3,4-b]pyrrolyl, octahydrocyclopenta[c]pyrrolyl, dihydroindolyl, azoniaspiro[4.5]decanyl, diazoniabicyclo[2.2.2]octanyl, diazoniabicyclo[2.2.1]heptanyl, diazoniabicyclo[3.2.1]octanyl, diazoniabicyclo[2.2.1]heptanyl, azoniabicyclo[3.1.0]hexanyl, tetrahydrothiophenyl, oxaazoniaspiro[4.5]decanyl and oxazepanyl.

As used herein, the term "halogen" refers to fluorine, chlorine, bromine and iodine, of which fluorine and chlorine are preferred.

Particular compounds within the scope of the present invention are:

2,2,2-trifluoro-1-[5-(3-{[(4-fluorobenzyl)sulfonyl]methyl}-1,2,4-oxadiazol-5-yl)-2-thienyl]ethanone;
1-{5-[5-(2-ethoxyphenyl)-1,3,4-oxadiazol-2-yl]-2-thienyl}-2,2,2-trifluoroethanone;
2,2,2-trifluoro-1-{5-[4-methylsulfinyl)phenyl]-2-thienyl}ethanone;
1-[5-(1-benzyl-1H-1,2,3-triazol-4-yl)-2-thienyl]-2,2,2-trifluoroethanone;
2,2,2-trifluoro-1-(4-quinoxalin-6-yl-2-thienyl)ethanone;
2,2,2-trifluoro-1-{5-[4-methylthio)phenyl]-2-thienyl}ethanone;
2,2,2-trifluoro-1-{5-[5-phenyl-1,3-thiazol-2-yl]-2-thienyl}ethanone;
2,2,2-trifluoro-1-(2-phenyl-1,3-thiazol-5-yl)ethanone;
2,2,2-trifluoro-1-[2-(2-naphthyl)-1,3-thiazol-5-yl]ethanone;
N-(4-fluorobenzyl)-5-(trifluoroacetyl)thiophene-2-carboxamide;
2,2,2-trifluoro-1-(5-{3-[(methylsulfonyl)methyl]-1,2,4-oxadiazol-5-yl}-2-thienyl)ethanone;
2,2,2-trifluoro-1-(5-{3-[(propylsulfonyl)methyl]-1,2,4-oxadiazol-5-yl}-2-thienyl)ethanone;
2,2,2-trifluoro-1-(5-{3-[(2-thienylsulfonyl)methyl]-1,2,4-oxadiazol-5-yl}-2-thienyl)ethanone;
1-[5-(3-{4-[(2,4-dichlorobenzyl)oxy]phenyl}-1,2,4-oxadiazol-5-yl)-2-thienyl]-2,2,2-trifluoroethanone;
1-{5-[3-(4-{[3-chloro-5-(trifluoromethyl)-2-pyridinyl]methoxy}benzyl)-1,2,4-oxadiazol-5-yl]-2-thienyl}-2,2,2-trifluoroethanone;
1-{5-{3-[3,5-bis(trifluoromethyl)benzyl]-1,2,4-oxadiazol-5-yl}-2-thienyl}-2,2,2-trifluoroethanone;
1-{5-[3-(2-chloro-4 fluorobenzyl)-1,2,4-oxadiazol-5-yl]-2-thienyl}-2,2,2-trifluoroethanone;
2,2,2-trifluoro-1-(5-{3-[3-(trifluoromethyl)phenyl]-1,2,4-oxadiazol-5-yl}-2-thienyl)ethanone;
2,2,2-trifluoro-1-(5-{3-[4-(trifluoromethoxy)phenyl]-1,2,4-oxadiazol-5-yl}-2-thienyl)ethanone;
2,2,2-trifluoro-1-{5-[3-(4-fluorophenyl)-1,2,4-oxadiazol-5-yl]-2-thienyl}ethanone;
1-{5-[3-(3-{[(4-chlorophenyl)sulfonyl]methyl}phenyl)-1,2,4-oxadiazol-5-yl]-2-thienyl}-2,2,2-trifluoroethanone;
3-({5-[5-(trifluoroacetyl)-2-thienyl]-1,2,4-oxadiazol-3-yl}methyl)-1,3-benzoxazol-2(3H)-one;
4-({5-[5-(trifluoroacetyl)-2-thienyl]-1,2,4-oxadiazol-3-yl}methyl)2H-1,4-benzoxazin-3(4H)-one;
1-(5-{3-[6-chloro-4-(phenylsulfonyl)-3,4-dihydro-2H-1,4-benzoxazin-2-yl]-1,2,4-oxadiazol-5-yl}-2-thienyl)-2,2,2-trifluoroethanone;
2,2,2-trifluoro-1-[5-(3-{4-[(2-methyl-1,3-thiazol-4-yl)methoxy]phenyl}-1,2,4-oxadiazol-5-yl)-2-thienyl]ethanone;
1-{5-[3-(2,4-difluorophenyl)-1,2,4-oxadiazol-5-yl]-2-thienyl}-2,2,2-trifluoroethanone;
2,2,2-trifluoro-1-{5-[3-(4-methoxyphenyl)-1,2,4-oxadiazol-5-yl]-2-thienyl}ethanone;
1-[5-(3-{4-[(4-chlorophenyl)sulfonyl]-3,4-dihydro-2H-1,4-benzoxazin-2-yl}-1,2,4-oxadiazol-5-yl)-2-thienyl]-2,2,2-trifluoroethanone;
2,2,2-trifluoro-1-{5-[3-(2-thienylmethyl)-1,2,4-oxadiazol-5-yl]-2-thienyl}ethanone;
N-(4-{5-[5-(2,2,2-trifluoroacetyl)-2-thienyl]-1,2,4-oxadiazol-3-yl}phenyl)acetamide;
2,2,2-trifluoro-1-[5-(3-{[4-(1,3,4-oxadiazol-2-yl)phenoxy]methyl}-1,2,4-oxadiazol-5-yl)-2-thienyl]ethanone;
2,2,2-trifluoro-1-{5-[3-(3-methylphenyl)-1,2,4-oxadiazol-5-yl]-2-thienyl}ethanone;
1-{5-[3-(4-bromo-1-methyl-1H-pyrazol-3-yl)-1,2,4-oxadiazol-5-yl]-2-thienyl}-2,2,2-trifluoroethanone;
2,2,2-trifluoro-1-{5-[3-(3-fluoro-4-methylphenyl)-1,2,4-oxadiazol-5-yl]-2-thienyl}ethanone;
2,2,2-trifluoro-1-[5-(3-methyl-1,2,4-oxadiazol-5-yl)-2-thienyl]ethanone;
2,2,2-trifluoro-1-{5-[5-(3-methoxyphenyl)-1,3,4-oxadiazol-2-yl]-2-thienyl}ethanone;
2,2,2-trifluoro-1-{5-[5-(4-fluorophenyl)-1,3,4-oxadiazol-2-yl]-2-thienyl}ethanone;
2,2,2-trifluoro-1-{5-[5-(2-furyl)-1,3,4-oxadiazol-2-yl]-2-thienyl}ethanone;
2,2,2-trifluoro-1-{5-[5-(2-thienyl)-1,3,4-oxadiazol-2-yl]-2-thienyl}ethanone;
2,2,2-trifluoro-1-[5-(5-phenyl-1,3,4-oxadiazol-2-yl)-2-thienyl]ethanone;
2,2,2-trifluoro-1-{5-[5-(4-methylphenyl)-1,3,4-oxadiazol-2-yl]-2-thienyl}ethanone;
1-{5-[5-(4-tert-butylphenyl)-1,3,4-oxadiazol-2-yl]-2-thienyl}-2,2,2-trifluoroethanone;
1-{5-[5-(1,3-benzodioxol-5-yl)-1,3,4-oxadiazol-2-yl]-2-thienyl}-2,2,2-trifluoroethanone;
1-{5-[5-(2,5-dimethoxyphenyl)-1,3,4-oxadiazol-2-yl]-2-thienyl}-2,2,2-trifluoroethanone;

2,2,2-trifluoro-1-{5-[5-(2-fluorophenyl)-1,3,4-oxadiazol-2-yl]-2-thienyl}ethanone;
1-{5-[5-(2-chlorophenyl)-1,3,4-oxadiazol-2-yl]-2-thienyl}-2,2,2-trifluoroethanone;
1-{5-[5-(4-chlorophenyl)-1,3,4-oxadiazol-2-yl]-2-thienyl}-2,2,2-trifluoroethanone;
1-{5-[5-(2,4-dichlorophenyl)-1,3,4-oxadiazol-2-yl]-2-thienyl}-2,2,2-trifluoroethanone;
2,2,2-trifluoro-1-[5-(3-phenyl-1,2,4-oxadiazol-5-yl)-2-thienyl]ethanone;
2,2,2-trifluoro-1-(5-pyridin-2-yl-2-thienyl)ethanone;
2,2,2-trifluoro-1-(5-quinoxalin-6-yl-2-thienyl)ethanone;
2,2,2-trifluoro-1-[5-(4-methoxyphenyl)-2-thienyl]ethanone;
2,2,2-trifluoro-1-[5-(4-phenoxyphenyl)-2-thienyl]ethanone;
2,2,2-trifluoro-1-[5-(2-methoxyphenyl)-2-thienyl]ethanone;
1-[5-(2,3-dihydro-1,4-benzodioxin-6-yl)-2-thienyl]-2,2,2-trifluoroethanone;
4-[5-(trifluoroacetyl)-2-thienyl]benzonitrile;
1-[5-(4-acetylphenyl)-2-thienyl]-2,2,2-trifluoroethanone;
2,2,2-trifluoro-1-{5-[3-(piperidin-1-ylcarbonyl)phenyl]-2-thienyl}ethanone;
2,2,2-trifluoro-1-[5-(1H-indol-5-yl)-2-thienyl]ethanone;
2,2,2-trifluoro-1-{5-[3-(1H-pyrazol-1-yl)phenyl]-2-thienyl}ethanone;
4-{3-[5-(trifluoroacetyl)-2-thienyl]benzyl}morpholin-4-ium trifluoroacetate;
2,2,2-trifluoro-1-[5-(3-methoxyphenyl)-2-thienyl]ethanone;
3-[5-(trifluoroacetyl)-2-thienyl]benzoic acid;
N,N-dimethyl{4-[5-(trifluoroacetyl)-2-thienyl]phenyl}methanaminium trifluoroacetate;
2,2,2-trifluoro-1-(5-quinolin-yl-2-thienyl)ethanone;
2,2,2-trifluoro-1-{5-[1-(2-naphthylmethyl)-1H-1,2,3-triazol-4-yl]-2-thienyl}ethanone;
1-{5-[1-(cyclohexylmethyl)-1H-1,2,3-triazol-4-yl]-2-thienyl}-2,2,2-trifluoroethanone;
2,2,2-trifluoro-1-{5-[3-(3-methylpyridin-2-yl)-1,2,4-oxadiazol-5-yl]-2-thienyl}ethanone;
2,2,2-trifluoro-1-[5-(3-pyridin-4-yl-1,2,4-oxadiazol-5-yl)-2-thienyl]ethanone;
2,2,2-trifluoro-1-[5-(3-pyridin-2-yl-1,2,4-oxadiazol-5-yl)-2-thienyl]ethanone;
2,2,2-trifluoro-1-(5-{3-[(phenylsulfonyl)methyl]-1,2,4-oxadiazol-5-yl}-2-thienyl)ethanone;
4-{5-[5-(trifluoroacetyl)-2-thienyl]-1,2,4-oxadiazol-3-yl}phenyl dimethylsulfamate;
2,2,2-trifluoro-1-[5-(3-{[(4-fluorophenyl)sulfonyl]methyl}-1,2,4-oxadiazol-5-yl)-2-thienyl]ethanone;
2,2,2-trifluoro-1-[5-(3-pyrazin-2-yl-1,2,4-oxadiazol-5-yl)-2-thienyl]ethanone;
2,2,2-trifluoro-1-{5-[3-(2-thienyl)-1,2,4-oxadiazol-5-yl]-2-thienyl}ethanone;
2,2,2-trifluoro-1-(5-{3-[6-(trifluoromethyl)pyridin-3-yl]-1,2,4-oxadiazol-5-yl}-2-thienyl)ethanone;
2,2,2-trifluoro-1-(5-{3-[4-(trifluoromethyl)phenyl]-1,2,4-oxadiazol-5-yl}-2-thienyl)ethanone;
2,2,2-trifluoro-1-[5-(3-pyridin-3-yl-1,2,4-oxadiazol-5-yl)-2-thienyl]ethanone;
2,2,2-trifluoro-1-{5-[3-(4-methylphenyl)-1,2,4-oxadiazol-5-yl]-2-thienyl}ethanone;
2,2,2-trifluoro-1-{5-[3-(2-oxo-2-pyrrolidin-1-ylethyl)-1,2,4-oxadiazol-5-yl]-2-thienyl}ethanol;
4-{5-[5-(trifluoroacetyl)-2-thienyl]-1,2,4-oxadiazol-3-yl}benzaldehyde;
2,2,2-trifluoro-1-(5-{3-[(isopropylsulfonyl)methyl]-1,2,4-oxadiazol-5-yl}-2-thienyl)ethanone;
1-{5-[3-(2,3-dihydro-1,4-benzodioxin-2-yl)-1,2,4-oxadiazol-5-yl]-2-thienyl}-2,2,2-trifluoroethanone;
1-{5-{3-[(4-tert-butylphenoxy)methyl]-1,2,4-oxadiazol-5-yl}-2-thienyl}-2,2,2-trifluoroethanone;
1-[5-(3-{[(4-chlorophenyl)sulfonyl]methyl}-1,2,4-oxadiazol-5-yl)-2-thienyl]-2,2,2-trifluoroethanone;
1-{5-[3-(2,4-dichlorophenyl)-1,2,4-oxadiazol-5-yl]-2-thienyl}-2,2,2-trifluoroethanone;
phenyl({5-[5-(trifluoroacetyl)-2-thienyl]-1,2,4-oxadiazol-3-yl}methyl)sulfoniumolate;
N-(3,4-dichlorophenyl)-2-{5-[5-(trifluoroacetyl)-2-thienyl]-1,2,4-oxadiazol-3-yl}acetamide;
2-morpholin-4-yl-5-[5-(trifluoroacetyl)-2-thienyl]pyridinium trifluoroacetate;
methyl 4-[5-(trifluoroacetyl)-2-thienyl]benzoate;
2,2,2-trifluoro-1-[5-(6-methoxypyridin-3-yl)-2-thienyl]ethanone;
2,2,2-trifluoro-1-(5-quinolin-8-yl-2-thienyl)ethanone;
2,2,2-trifluoro-1-(5-quinolin-3-yl-2-thienyl)ethanone;
1-{5-[3-(3,5-dimethyl-1H-pyrazol-1-yl)phenyl]-2-thienyl}-2,2,2-trifluoroethanone;
1-[5-(1-benzothien-7-yl)-2-thienyl]-2,2,2-trifluoroethanone;
2,2,2-trifluoro-1-{5-[4-(1H-pyrazol-1-yl)phenyl]-2-thienyl}ethanone;
N-methyl-N-(quinoxalin-6-ylmethyl)-3-[5-(trifluoroacetyl)-2-thienyl]benzamide;
2,2,2-trifluoro-1-[5-(4-nitrophenyl)-2-thienyl]ethanone;
2,2,2-trifluoro-1-{5-[4-(trifluoromethyl)phenyl]-2-thienyl}ethanone;
2,2,2-trifluoro-1-[5-(1H-pyrazol-3-yl)-2-thienyl]ethanone;
5-[5-(trifluoroacetyl)-2-thienyl]isoquinolinium trifluoroacetate;
2,2,2-trifluoro-1-(5-pyrimidin-5-yl-2-thienyl)ethanone;
1-[5-(1-benzothien-3-yl)-2-thienyl]-2,2,2-trifluoroethanone;
2,2,2-trifluoro-1-[5-(4-isopropoxyphenyl)-2-thienyl]ethanone;
N-{4-[5-(2,2,2-trifluoroacetyl)-2-thienyl]phenyl}acetamide;
1-[5-(1,3-benzodioxol-5-yl)-2-thienyl]-2,2,2-trifluoroethanone;
N-{4-[5-(2,2,2-trifluoroacetyl)-2-thienyl]phenyl}methanesulfonamide;
tert-butyl {3-[5-(trifluoroacetyl)-2-thienyl]phenyl}carbamate;
2,2,2-trifluoro-1-{5-[1-(4-methylbenzyl)-1H-1,2,3-triazol-4-yl]-2-thienyl}ethanone;
4-{4-[5-(trifluoroacetyl)-2-thienyl]-1H-1,2,3-triazol-1-yl}methyl)benzonitrile
2,2,2-trifluoro-1-{1-[4-(methylsulfonyl)benzyl]-1H-1,2,3-triazol-4-yl}-2-thienyl)ethanone;
2,2,2-trifluoro-1-[5-(1-{2-[(phenylsulfonyl)methyl]benzyl}-1H-1,2,3-triazol-4-yl)-2-thienyl]ethanone;
1-{5-[1-(1,3-benzothiazol-2-ylmethyl)-1H-1,2,3-triazol-4-yl]-2-thienyl}-2,2,2-trifluoroethanone;
1-{5-[1-(cyclobutylmethyl)-1H-1,2,3-triazol-4-yl]-2-thienyl}-2,2,2-trifluoroethanone;
4-[5-(trifluoroacetyl)-2-thienyl]benzoic acid;
N-(4-fluorobenzyl)-3-[5-(trifluoroacetyl)-2-thienyl]benzamide;
N-methyl-N-(quinoxalin-6-ylmethyl)-4-[5-(trifluoroacetyl)-2-thienyl]benzamide;
(2E)-3-{4-[5-(trifluoroacetyl)-2-thienyl]phenyl}acrylic acid;
(2E)-3-{3-[5-(trifluoroacetyl)-2-thienyl]phenyl}acrylic acid;
1-[5-(4-benzoylphenyl)-2-thienyl]-2,2,2-trifluoroethanone;
2,2,2-trifluoro-1-(5-pyridin-3-yl-2-thienyl)ethanone;
2,2,2-trifluoro-1-{5-[2-(1H-pyrazol-1-yl)phenyl]-2-thienyl}ethanone;

(2E)-N-methyl-N-(quinoxalin-6-ylmethyl)-3-{4-[5-(trifluoroacetyl)-2-thienyl]phenyl}acrylamide;
(2E)-N-(4-fluorobenzyl)-3-{4-[5-(trifluoroacetyl)-2-thienyl]phenyl}acrylamide;
(2E)-N-methyl-N-(quinoxalin-6-ylmethyl)-3-{3-[5-(trifluoroacetyl)-2-thienyl]phenyl}acrylamide;
(2E)-N-(4-fluorobenzyl)-3-{3-[5-(trifluoroacetyl)-2-thienyl]phenyl}acrylamide;
4-[5-(trifluoroacetyl)-1,3-thiazol-2-yl]pyridinium trifluoroacetate;
1-[2-(4-acetylphenyl)-1,3-thiazol-5-yl]-2,2,2-trifluoroethanone;
2,2,2-trifluoro-1-[2-(1-naphthyl)-1,3-thiazol-5-yl]ethanone;
4-[5-(trifluoroacetyl)-1,3-thiazol-2-yl]benzonitrile;
2,2,2-trifluoro-1-[2-(4-phenoxyphenyl)-1,3-thiazol-5-yl]ethanone;
1-(2-biphenyl-4-yl-1,3-thiazol-5-yl)-2,2,2-trifluoroethanone;
2,2,2-trifluoro-1-{2-[4-(trifluoromethyl)phenyl]-1,3-thiazol-5-yl}ethanone;
2,2,2-trifluoro-1-[2-(4-nitrophenyl)-1,3-thiazol-5-yl]ethanone;
1-[2-(3,4-dichlorophenyl)-1,3-thiazol-5-yl]-2,2,2-trifluoroethanone;
1-[2-(4-bromophenyl)-1,3-thiazol-5-yl]-2,2,2-trifluoroethanone;
1-[2-(3,4-difluorophenyl)-1,3-thiazol-5-yl]-2,2,2-trifluoroethanone;
2,2,2-trifluoro-1-(5-thianthren-1-yl-2-thienyl)ethanone;
1-[5-(2,3-dihydro-1-benzofuran-5-yl)-2-thienyl]-2,2,2-trifluoroethanone;
tert-butyl {4-[5-(trifluoroacetyl)-2-thienyl]phenyl}carbamate; and
2,2,2-trifluoro-1-(5-phenyl-2-thienyl)ethanone.

Included in the instant invention is the free base of compounds of Formula I, as well as the pharmaceutically acceptable salts and stereoisomers thereof. Some of the specific compounds exemplified herein are the protonated salts of amine compounds. Compounds of Formula I with a heterocycle ring containing 2 or more N atoms may be protonated on any one, some or all of the N atoms. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Preferably, a pharmaceutically acceptable salt of this invention contains 1 equivalent of a compound of formula (I) and 1, 2 or 3 equivalent of an inorganic or organic acid. More particularly, pharmaceutically acceptable salts of this invention are the trifluoroacetate or the chloride salts, especially the trifluoroacetate salts.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N'-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al (1977) *J. Pharm. Sci., 'Pharmaceutical Salts'* 66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the invention can be used in a method of treatment of the human or animal body by therapy.

The compounds of the invention find use in a variety of applications for human and animal health. The compounds of the invention are histone deacetylase (HDAC) inhibitors useful in the treatment of cancer among other diseases. HDACs catalyse the removal of acetyl groups from lysine residues on proteins, including histones and HDAC inhibitors show diverse biological functions including affecting gene expression, cell differentiation, cell cycle progression, growth arrest, and/or apoptosis. See *J. Med. Chem.* (2003) 46:5097 and *Curr. Med. Chem.* (2003) 10:2343.

The compounds of the invention are used to treat cellular proliferation diseases. Disease states which can be treated by the methods and compositions provided herein include, but are not limited to, cancer (further discussed below), neurodegenerative diseases, schizophrenia and stroke.

The compounds, compositions and methods provided herein are particularly deemed useful for the treatment of cancer including solid tumors such as skin, breast, brain, cervical carcinomas, testicular carcinomas, etc. In particular, cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, prtumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Thus, the present invention provides a compound of formula I for use in the manufacture of a medicament for treating cellular proliferation diseases.

The present invention also provides a method for the treatment of cellular proliferation diseases, which method comprises administration to a patient in need thereof of an effective amount of a compound of formula I or a composition comprising a compound of formula I.

The compounds of the instant invention may also be useful in the treatment or prevention of neurodegenerative diseases, including, but not limited to, polyglutamine-expansion-related neurodegeneration, Huntington's disease, Kennedy's disease, spinocerebellar ataxia, dentatorubral-pallidoluysian atrophy (DRPLA), protein-aggregation-related neurodegeneration, Machado-Joseph's disease, Alzheimer's disease, Parkinson's disease, amyotrophic lateral sclerosis, spongiform encephalopathy, a prion-related disease and multiple sclerosis (MS). See WO 02/090534 and WO 03/083067.

Thus, the present invention provides a compound of formula I for use in the manufacture of a medicament for treating or preventing neurodegenerative diseases.

The present invention also provides a method for treating or preventing neurodegenerative diseases, which method comprises administration to a patient in need thereof of an effective amount of a compound of formula I or a composition comprising a compound of formula I.

The compounds of the invention may also be useful in the treatment or prevention of mental retardation, in particular "X chromosome-linked mental retardation" and "Rubinstein-Taybi syndrome".

Thus, the present invention provides a compound of formula I for the manufacture of a medicament for treating or preventing mental retardation.

The present invention also provides a method for treating or preventing mental retardation, which method comprises administration to a patient in need thereof of an effective amount of a compound of formula I or a composition comprising a compound of formula I.

The compounds of the invention may also be useful in the treatment or prevention of schizophrenia, see WO 02/090534.

Thus, the present invention provides a compound of formula I for the manufacture of a medicament for treating or preventing schizophrenia.

The present invention also provides a method for treating or preventing schizophrenia, which method comprises administration to a patient in need thereof of an effective amount of a compound of formula I or a composition comprising a compound of formula I.

The compounds of the invention may also be useful in the treatment or prevention of inflammatory diseases, including, but not limited to stroke, rheumatoid arthritis, lupus erythematosus, ulcerative colitis and traumatic brain injuries. See Leoni et al (2002), *PNAS*, 99(5):2995-3000, Suuronen et al. (2003) *J. Neurochem*, 87:407-416 and *Drug Discovery Today* (2005), 10:197-204.

Thus, the present invention provides a compound of formula I for the manufacture of a medicament for treating or preventing inflammatory diseases.

The present invention also provides a method for treating or preventing inflammatory diseases, which method comprises administration to a patient in need thereof of an effective amount of a compound of formula I or a composition comprising a compound of formula I.

The compounds of the present invention are also useful in the inhibition of smooth muscle cell proliferation and/or migration and are thus useful in the prevention and/or treatment of restenosis, for example after angioplasty and/or stent implantation.

Thus, the present invention provides a compound of formula I for the manufacture of a medicament for treating or preventing restenosis.

The present invention also provides a method for treating or prevention restenosis, which method comprises administration to a patient in need thereof of an effective amount of a compound of formula I or a composition comprising a compound of formula I.

In one embodiment, smooth muscle cell proliferation and/or migration is inhibited and restenosis is prevented and/or treated by providing a stent device having one or more of the compounds of the instant invention in or on the stent device, e.g. coated onto the stent device. The stent device is designed to controllably release the compounds of the invention, thereby inhibiting smooth miscle cell proliferation and/or migration and preventing and/or treating restenosis.

Stenosis and restenosis are conditions associated with a narrowing of blood vessels. Stenosis of blood vessels generally occurs gradually over time. Restenosis, in contrast, relates to a narrowing of blood vessels following an endovascular procedure, such as balloon angioplasty and/or stent implantation, or a vascular injury.

Balloon angioplasty is typically performed to open a stenotic blood vessel; stenting is usually performed to maintain the patency of a blood vessel after, or in combination with, balloon angioplasty. A stenotic blood vessel is opened with balloon angioplasty by navigating a balloon-tipped catheter to the site of stenosis, and expanding the balloon tip effectively to dilate the occluded blood vessel. In an effort to maintain the patency of the dilated blood vessel, a stent may be implanted in the blood vessel to provide intravascular support to the opened section of the blood vessel, thereby limiting the extent to which the blood vessel will return to its occluded state after release of the balloon catheter. Restenosis is typically caused by trauma inflicted during angioplasty, effected by, for example, balloon dilation, atherectomy or laser ablation treatment of the artery. For these procedures, restenosis occurs at a rate of about 30% to about 60% depending on the vessel location, lesion length and a number of other variables. This reduces the overall success of the relatively non-invasive balloon angioplasty and stenting procedures.

Restenosis is attributed to many factors, including proliferation of smooth muscle cells (SMC). SMC proliferation is triggered by the initial mechanical injury to the intima that is sustained at the time of balloon angioplasty and stent implantation. The process is characterized by early platelet activation and thrombus formation, followed by SMC recruitment and migration, and, finally, cellular proliferation and extracellular matrix accumulation. Damaged endothelial cells, SMCs, platelets, and macrophages secrete cytokines and growth factors which promote restenosis. SMC proliferation represents the final common pathway leading to neointimal hyperplasia. Therefore, anti-proliferative therapies aimed at inhibiting specific regulatory events in the cell cycle may constitute the most reasonable approach to restenosis after angioplasty.

The compounds of the invention may also be used as immunosuppressants or immunomodulators and can accordingly be used in the treatment or prevention of immune response or immune-mediated responses and diseases such as systemic lupus erythematosus (SLE) and acute or chronic transplant rejection in a recipient of an organ, tissue or cell transplant, (see WO 05/013958).

Examples of autoimmune diseases for which the compounds of the invention may be employed include autoimmune hematological disorders (including hemolytic anaemia, aplastic anaemia, pure red cell anaemia and idiopathic thrombocytopenia), systemic lupus erythematosus, thyroiditis, Hashimoto's thyroiditis, polychondritis, sclerodoma, Wegener granulamatosis, dermatomyositis, chronic active hepatitis, myasthenia gravis, psoriasis, atopic dermatitis, vasculitis, Steven-Johnson syndrome, idiopathic sprue, autoimmune inflammatory bowel disease (including ulcerative colitis and Crohn's disease) endocrine opthalmopathy, Graves disease, sarcoidosis, multiple sclerosis, primary billiary cirrhosis, juvenile diabetes (diabetes mellitus type I), diabetes type II and the disorders associated therewith, uveitis (anterior and posterior), keratoconjunctivitis sicca and vernal keratoconjunctivitis, interstitial lung fibrosis, psoriatic arthritis, glomerulonephritis (with and without nephrotic syndrome, including idiopathic nephrotic syndrome or minimal change nephropathy), juvenile dermatomyositis infectious, auto-antibody mediated diseases, aplastic anemia, Evan's syndrome, autoimmune hemolytic anemia, infectious diseases causing aberrant immune response and/or activation, such as traumatic or pathogen induced immune disregulation, including for example, that which are caused by hepatitis B and C infections, *staphylococcus aureus* infection, viral encephalitis, sepsis, parasitic diseases wherein damage is induced by inflammatory response (e.g. leprosy); and circulatory diseases, such as arteriosclerosis, atherosclerosis, polyarteritis nodosa and myocarditis.

Thus, the present invention provides a compound of formula I for the manufacture of a medicament for the treatment or prevention of immune disorders.

The present invention also provides a method for treating or preventing immune disorders, which method comprises administration to a patent in need thereof of an effective amount of a compound of formula I or a composition comprising a compound of formula I.

The compounds of the invention may also be useful in the treatment or prevention of other diseases such as diabetes, cardiovascular disorders, asthma, cardiac hypertrophy and heart failure, (see *Cell* (2002), 110:479-488).

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid;

binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intrenasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing treatment for cancer. Administration generally occurs in an amount between about 0.1 mg/kg of body weight to about 60 mg/kg of body weight per day, preferably of between 0.5 mg/kg of body weight to about 40 mg/kg of body weight per day.

The instant compounds are also useful in combination with known therapeutic agents and anti-cancer agents. Thus, this invention provides combinations of compounds of formula (I) and known therapeutic agents and/or anti-cancer agents for simultaneous, separate or sequential administration. For example, instant compounds are useful in combination with known anti-cancer agents. Combinations of the presently disclosed compounds with other anticancer or chemotherapeutic agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: other HDAC inhibitors, estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The instant compounds are particularly useful when co-administered with radiation therapy.

In an embodiment, the instant compounds are also useful in combination with known anti-cancer agents including the following: other HDAC inhibitors, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

Examples of "other HDAC inhibitors" include suberoylanilide hydroxamic acid (SAHA), LAQ824, LBH589, PXD101, MS275, FK228, valproic acid, butyric acid and CI-994.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell mytosis, including alkylating agents, tumor necrosis factors, intercalators, hypoxia activatable compounds, microtubule inhibitors/microtubule-stabilizing agents, inhibitors of mitotic kinesins, inhibitors of kinases involved in mitotic progression, antimetabolites; biological response modifiers; hormonal/anti-hormonal therapeutic agents, haematopoietic growth factors, monoclonal antibody targeted therapeutic agents, topoisomerase inhibitors, proteasome inhibitors and ubiquitin ligase inhibitors.

Examples of cytotoxic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum (II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinylmethylsulphonyl-daunorubicin (see WO 00/50032).

An example of a hypoxia activatable compound is tirapazanine.

Examples of proteasome inhibitors include but are not limited to lactacystin, bortezomib, epoxomicin and peptide aldehydes such as MG 132, MG 115 and PSI.

In an embodiment, the compounds of the present invention may be used in combination with other HDAC inhibitors such as SAHA and proteasome inhibitors.

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5, 6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB, 8aa,9b)-9-[2-[N-[2-dimethylamino)ethyl]-N-methylamino] ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoquinoline-5,10-done, 5-(3-aminopropylamino)-7,10-dihydroxy-2-(2-hydroxyethylaminomethyl)-6H-pyrazolo[4,5,1-de]acridin-6-one, N-[1-[2-(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in PCT Publications WO 01/30768, WO 01/98278, WO 02/056880, WO 03/050,064, WO 03/050,122, WO 03/049,527, WO 03/049,679, WO 03/049,678, WO 03/039460, WO 03/079973, WO 03/099211, WO 2004/039774, WO 03/105855, WO 03/106417, WO 2004/087050, WO 2004/058700, WO 2004/058148 and WO 2004/037171 and US applications US 2004/132830 and US 2004/132719. In an embodiment inhibitors of mitotic kinesins include, but are not limited to inhibitors of KSP, inhibitors of MKLP1, inhibitors of CENP-E, inhibitors of MCAK, inhibitors of Kif14, inhibitors of Mphosph1 and inhibitors of Rab6-KIFL.

"Inhibitors of kinases involved in mitotic progression" include, but are not limited to, inhibitors of aurora kinase, inhibitors of Polo-like kinases (PLK) (in particular inhibitors of PLK-1), inhibitors of bub-1 and inhibitors of bub-R1.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine and 3-aminopyridine-2-carboxaldehyde thiosemicarbazone.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916, 239), pravastatin (PRAVACHOL®; see U.S. Pat. Nos. 4,346, 227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896) and atorvastatin (LIPITOR®; see U.S. Pat. Nos. 5,273, 995, 4,681,893, 5,489,691 and 5,342,952). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefore the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359.

For an example of the role of a prenyl-protein transferase inhibitor on angiogenesis see *European J. of Cancer* (1999), 35(9):1394-1401.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS (1992) 89:7384; JNCI (1982) 69:475; *Arch. Opthalmol.* (1990) 108: 573; *Anat. Rec.* (1994) 238:68; *FEBS Letters* (1995) 372:83; *Clin, Orthop.* (1995) 313:76; *J. Mol. Endocrinol.* (1996) 16:107; *Jpn. J. Pharmacol.* (1997) 75:105; *Cancer Res.* (1997) 57:1625 (1997); *Cell* (1998) 93:705; *Intl. J. Mol. Med.* (1998) 2:715; *J. Biol. Chem.* (1999) 274:9116)), steroidal anti-inflammatories (such as corticosteroids, mineralocorticoids, dexarethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al (1985) *J. Lab. Clin. Med.* 105:141-145), and antibodies to VEGF (see, *Nature Biotechnology* (1999) 17:963-968; Kim et al (1993) *Nature* 362:841-844; WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* (2000) 38:679-692). Examples of such agents that modulate or inhibit the coagulation and fibrinolysis pathways include, but are not limited to, heparin (see *Thromb. Haemost.* (1998) 80:10-23), low molecular weight heparins and carboxypeptidase U inhibitors (also known as inhibitors of active thrombin activatable fibrinolysis inhibitor [TAFIa]) (see *Thrombosis Res.* (2001) 101:329-354). TAFIa inhibitors have been described in PCT Publication WO 03/013,526 and U.S. Ser. No. 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the Chk1 and Chk2 kinases and cdk and cdc kinase inhibitors and are specifically exemplified by 7-hydroxystaurosporin, flavopiridol, CYC202 (Cyclacel) and BMS-387032.

"Inhibitors of cell proliferation and survival signaling pathway" refer to pharmaceutical agents that inhibit cell surface receptors and signal transduction cascades downstream of those surface receptors. Such agents include inhibitors of inhibitors of EGFR (for example gefitinib and erlotinib), inhibitors of ERB-2 (for example trastuzumab), inhibitors of IGFR (for example those disclosed in WO 03/059951), inhibitors of cytokine receptors, inhibitors of MET, inhibitors of PI3K (for example LY294002), serine/threonine kinases (including but not limited to inhibitors of Akt such as described in (WO 03/086404, WO 03/086403, WO 03/086394, WO 03/086279, WO 02/083675, WO 02/083139, WO 02/083140 and WO 02/083138), inhibitors of Raf kinase (for example BAY43-9006), inhibitors of MEK (for example CI-1040 and PD-098059) and inhibitors of mTOR (for example Wyeth CCI-779 and Ariad AP23573). Such agents include small molecule inhibitor compounds and antibody antagonists.

"Apoptosis inducing agents" include activators of TNF receptor family members (including the TRAIL receptors).

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550, 142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823, U.S. Pat. No. 5,633, 272, and U.S. Pat. No. 5,932,598, all of which are hereby incorporated by reference.

Inhibitors of COX-2 that are particularly useful in the instant method of treatment are 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to: parecoxib, CELEBREX® and BEXTRA® or a pharmaceutically acceptable salt thereof.

Other examples of angiogenesis inhibitors include, but are not limited to, endostatin, ukrain, ranpimase, IM862, 5-methoxy-4-[2-methyl-3-(3-methyl-2-butenyl)oxiranyl]-1-oxaspiro[2,5]oct-yl(chloroacetyl)carbamate, acetyldinanaline, 5-amino-1-[[3,5-dichloro-4-(4-chlorobenzoyl)phenyl]methyl]-1H-1,2,3-triazole carboxamide, CM101, squalamine, combretastatin, RPI4610, NX31838, sulfated mannopentaose phosphate, 7,7-carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$ $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\beta_5\alpha_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9, 10,11,12-hexahydro-10-(hydroxymethyl)-10-hydroxy-9-methyl-9,12-epoxy-1H-diindolo[1,2,3-fg:3',2',1'-kl]pyrrolo [3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinaoline, 4-(4'-hydroxyphenyl)amino-6,7-dimethoxyquinazoline, SU6668, STI571A, N-4-chlorophenyl (4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* (1998) 31:909-913; *J. Biol. Chem.* (1999) 274: 9116-9121; *Invest. Opthalmol. Vis. Sci.* (2000) 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* (2001) 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. Nos. 60/235,708 and 60/244,697).

Another embodiment of the instant invention is the use of the presently disclosed compounds in combination with antiviral agents (such as nucleoside analogs including ganciclovir for the treatment of cancer. See WO 98/04290.

Another embodiment of the instant invention is the use of the presently disclosed compounds in combination with gene therapy for the treatment of cancer. For an overview of genetic strategies to treating cancer see Hall et al (*Am J Hum Genet* (1997) 61:785-789) and Kufe et al (*Cancer Medicine*, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," *Gene Therapy*, August (1998) 5(8):1105-13), and interferon gamma (*J Immunol* (2000) 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, $GABA_B$ receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In an embodiment, an anti-emesis agent selected from a neurokinin-1 receptor antagonist, a 5HT3 receptor antagonist and a corticosteroid is administered as an adjuvant for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232, 929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585,92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include fligrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

Thus, the scope of the instant invention encompasses the use of the instantly claimed compounds in combination with a second compound selected from: other HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

In an embodiment, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an embodiment, the estrogen receptor modulator is tamoxifen or raloxifene.

Also included in the scope of the claims is a method of treating cancer that comprises administering a therapeutically effective amount of a compound of Formula I in combination with radiation therapy and/or in combination with a compound selected from: other HDAC inhibitors, an estrogen receptor modulator, an androgen receptor modulator, retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, an agent that interfers with a cell cycle checkpoint, an apoptosis inducing agent and a bisphosphonate.

And yet another embodiment of the invention is a method of treating cancer that comprises administering a therapeutically effective amount of a compound of Formula I in combination with paclitaxel or trastuzumab.

The invention further encompasses a method of treating or preventing cancer that comprises administering a therapeutically effective amount of a compound of Formula I in combination with a COX-2 inhibitor.

The instant invention also includes a pharmaceutical composition useful for treating or preventing cancer that comprises a therapeutically effective amount of a compound of Formula I and a compound selected from: other HDAC inhibitors, an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an anti-viral agent, an inhibitor of cell proliferation and survival signaling, an agent that interfers with a cell cycle checkpoint, an apoptosis inducing agent and a bisphosphonate.

These and other aspects of the invention will be apparent from the teachings contained herein.

Abbreviations used in the description of the chemistry and in the Examples that follow are:

Aq: aqueous; DMF: dimethylformamide; DMSO: dimethylsulfoxide; MeOH: methanol; EtOAc: ethyl acetate; PE: petroleum ether; THF: tetrahydrofuran; DCM: dichloromethane; CHCl$_3$: chloroform; CD$_3$CN: acetonitrile-d$_3$; CDCl$_3$:

chloroform-d; CDI: carbonyldiimidazole; HCl: hydrogen chloride; min: minutes; h: hour(s); eq.: equivalent(s); M: molar; RT: room temperature; O/N: overnight; RP-HPLC: reversed phase high-pressure liquid chromatography; BuLi: butyllithium; LDA: lithium diisopropylamide; EDCl: 1-(3-dimethylaminopropyl-3-ethylcarbodiimide hydrochloride; HOBt: 1-hydroxybenzotriazole; Sat: saturated; TMSCF$_3$: trimethyl(trifluoromethyl)silane; and PS-CDI: polymer supported carbodiimide.

Compounds of formula I wherein X is 1,2,4-oxadiazole can be prepared by reacting a compound of formula IA with an appropriate dehydrating agent, such as CDI:

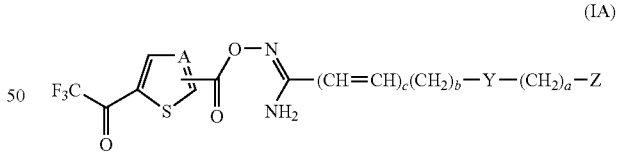

(IA)

wherein a, b, c, A, Y and Z are as defined above, generally at a temperature of about 140° C. and in a solvent such as DMF.

Compounds of formula IA can be prepared by reacting a compound of formula IB with a compound of formula IC:

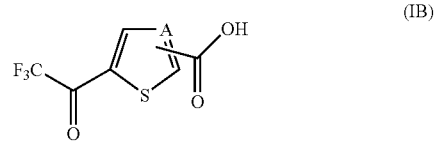

(IB)

-continued

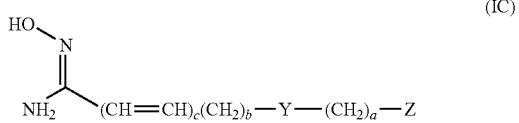
(IC)

wherein a, b, c, A, Y and Z are so defined above. An appropriate activating agent such as CDI can generally be used, in a solvent such as DMF at about room temperature.

The carboxylic acid of formula IB can appropriately be formed by hydrolysis of the corresponding ester. Standard hydrolysis conditions can be used, such as by the addition of a base such as LiOH, generally in solvents such as methanol and water at about room temperature.

Compounds of formula I wherein X is 1,3,4-oxadiazole can be prepared by reacting a compound of formula ID with an appropriate dehydrating agent, such as thionyl chloride:

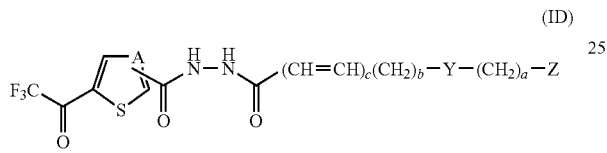
(ID)

wherein a, b, c, A, Y and Z are as defined above, generally at a temperature of about 100° C.

Compounds of formula ID can be prepared by reacting a compound of formula IB with a compound of formula IE:

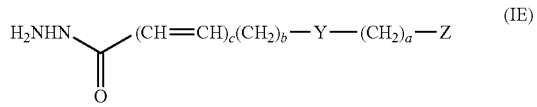
(IE)

wherein a, b, c, Y and Z are as defined above. An appropriate activating agent such as CDI can generally be used, in solvents such as DCM and DMF at about room temperature.

Compounds of formula I can alternatively be prepared by reacting a compound of formula IF with a compound of formula IG:

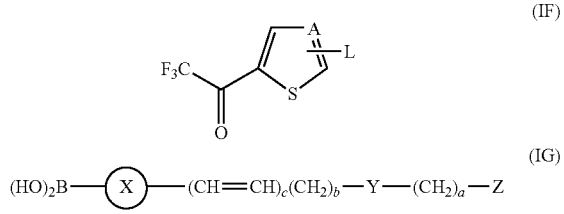
(IF)

(IG)

wherein a, b, c, A, Y and Z are as defined above and L is a leaving group such as halogen, for example bromine. The reaction is generally carried out in the presence of a coupling agent such as Pd(PPh$_3$)$_4$, a base such as Na$_2$CO$_3$ or K$_2$CO$_3$ and in a solvent such as DMF or ethanol at about 75° C. to 90° C.

Compounds of formula IF can be prepared by oxidizing the compound of formula IH:

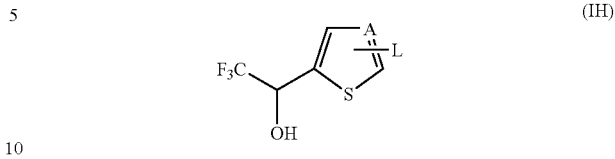
(IH)

wherein A and L are as defined above. Standard oxidizing conditions can be used, such as the use of a Dess-Martin reagent, in a solvent such as DCM at about room temperature.

Compounds of formula IH can be prepared by reacting a compound of formula IJ with an appropriate trifluoroacetyl source, such as TMSCF$_3$ in the presence of CsF:

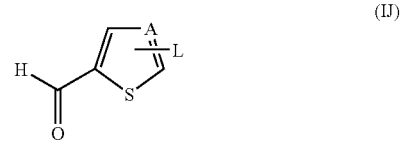
(IJ)

wherein A and L are as defined above, generally at about room temperature.

Alternatively, compounds of formula I can be prepared by reacting a compound of formula IG, or a related derivative like a boronate ester, with a compound of formula IH. The reaction is generally carried out in the presence of a coupling agent such as Pd(PPh$_3$)$_4$, a base such as Na$_2$CO$_3$ and in a solvent such as DMF at about 90° C. The trifluoroalkylethanol moiety can subsequently be oxidised to trifluoroalkylethanone under standard oxidizing conditions as previously described.

Compounds of formula I wherein X is 1,2,3-triazole can be prepared by reacting a compound of formula IK with a compound of formula IL:

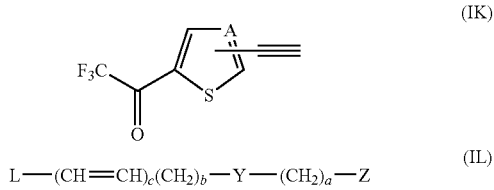
(IK)

(IL)

wherein a, b, c, A, Y, Z and L are as defined above, in the presence of sodium azide. The reaction is generally carried out using catalysts such as copper, for example in the form of copper powder and copper sulfate, in solvents such as t-butanol and water at about 125° C. in a microwave.

Compounds of formula IK can be prepared by reacting a compound of formula IF with a compound of formula IM:

(IM)

wherein P is an appropriate protecting group such as trimethysilyl, generally in the presence of coupling agents such as Pd(PPh$_3$)$_2$Cl$_2$ and CuI, a base such as NEt$_3$ and a solvent such as THF at about room temperature. Deprotection can be carried out under standard condition, such as by the use of a base such as LiOH in water and THF at about room temperature.

Compounds of formula I wherein X is thiazole can be prepared by reacting a compound of formula IN with a cyclising agent such as a Lawesson's reagent:

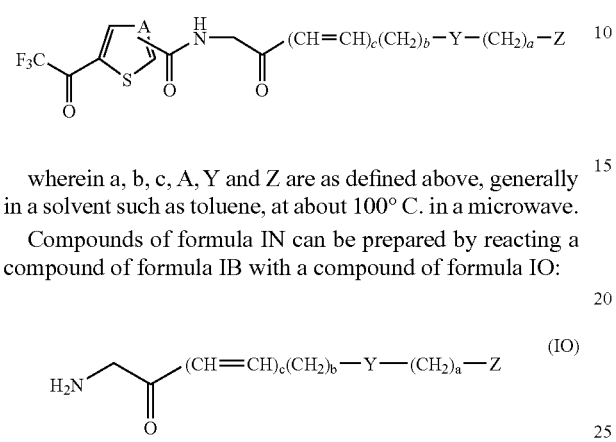

(IN)

wherein a, b, c, A, Y and Z are as defined above, generally in a solvent such as toluene, at about 100° C. in a microwave.

Compounds of formula IN can be prepared by reacting a compound of formula IB with a compound of formula IO:

(IO)

wherein a, b, c, Y and Z are as defined above. An appropriate activating agent such as carbodiimide can generally be used, in a solvent such as DCM at about room temperature. A base such as $NEt_3$ may also be added.

Where the synthesis of intermediates and starting materials is not described, these compounds are commercially available or can be made from commercially available compounds by standard methods or by extension of the Examples herein.

Compounds of formula I may be converted to other compounds of formula I by known methods or by methods described in the Examples.

During any of the synthetic sequences described herein it may be necessary and/or desirable to protect sensitive or reactive groups on any of the molecules concerned. This may be achieved by means of conventional protecting groups, such as those described in *Protecting Groups in Organic Synthesis*, 3rd Edition, Greene, T. W. and Wuts, P. G. M.; Wiley Interscience, 1999 and Kocienski, P. J. Protecting Groups, Thieme, 1994. The protecting groups may be removed at a convenient subsequent stage using methods known from the art.

The compounds of this invention were prepared according to the following schemes. All variables within the formulae are as defined above.

Schemes

The desired HDAC inhibitors can be prepared by those skilled in the art using the general procedures detailed below. For instance, to enable 1,2,4-oxadiazoles to be prepared the 5-(trifluoroacetyl)thiophene-2-carboxylic acid, readily obtainable through basic hydrolysis of the corresponding ethyl ester, can be activated. Suitable activation methods include the formation of the acyl imidazole by treatment with carbonyldiimidazole. The resulting species can then be reacted with an amidoxime and cyclised under dehydrative condition such as treatment with further carbonyldiimidazole under microwave heating (Scheme 1).

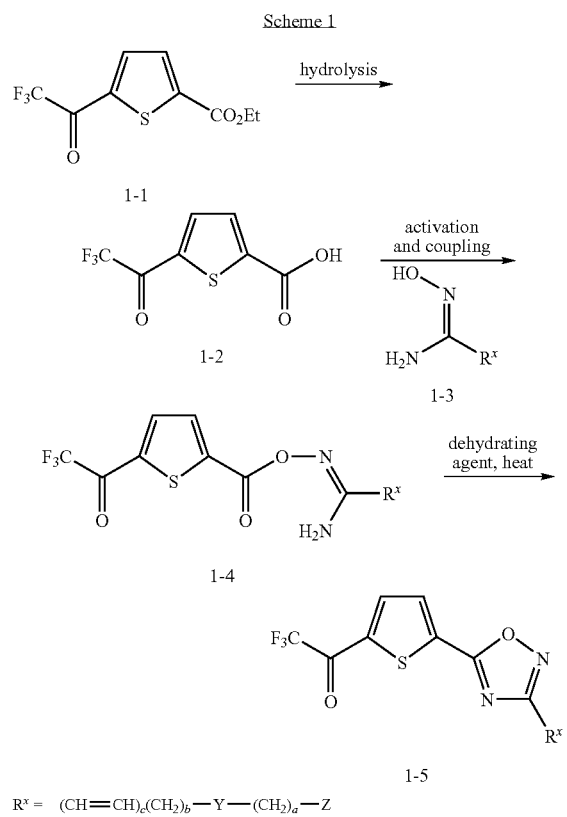

$R^x = (CH=CH)_c(CH_2)_b-Y-(CH_2)_a-Z$

Alternatively, to prepare 1,3,4-oxadiazoles the activated carboxylic acid can be reacted with an acyl hydrazide and again cyclised under dehydrative condition, such as using thionyl chloride under microwave heating (Scheme 2).

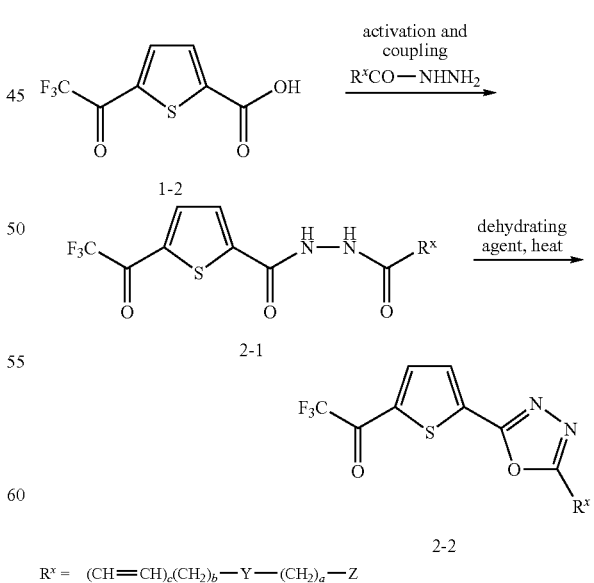

$R^x = (CH=CH)_c(CH_2)_b-Y-(CH_2)_a-Z$

An alternative procedure to synthesise the desired inhibitors is to utilize palladium cross-coupling chemistry as shown in scheme 3. Here a functionalised heterocyclic bromide can be prepared from the corresponding aldehyde by addition of a trifluoromethyl group, for instance by addition of trimethyl (trifluoromethyl)silane using cesium fluoride, followed by subsequent oxidation with reagents such as Dess-Martin reagent to give the key building block. Suzuki cross-coupling of this bromide with a boronic acid in the presence of palladium catalysis and a base yields the desired inhibitors. This can also be performed using polymer support catalysts.

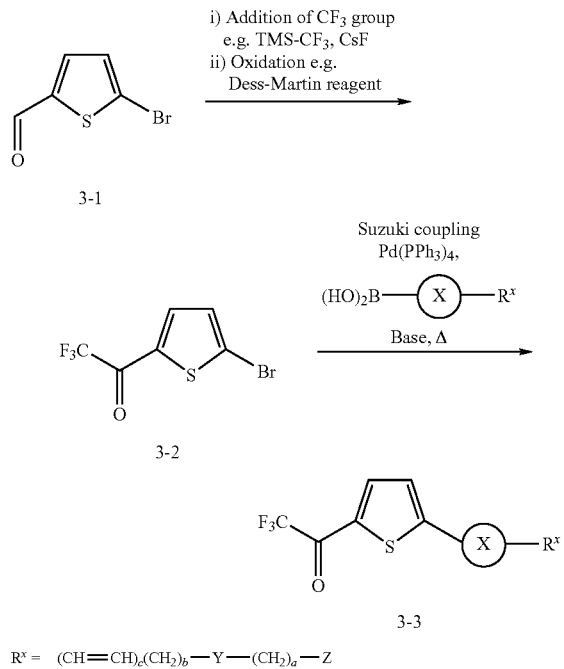

A similar procedure can be used to obtain thiophene derivatives functionalised in the C-4 position as shown in scheme 4. Here the palladium cross-coupling is performed prior to the final oxidation.

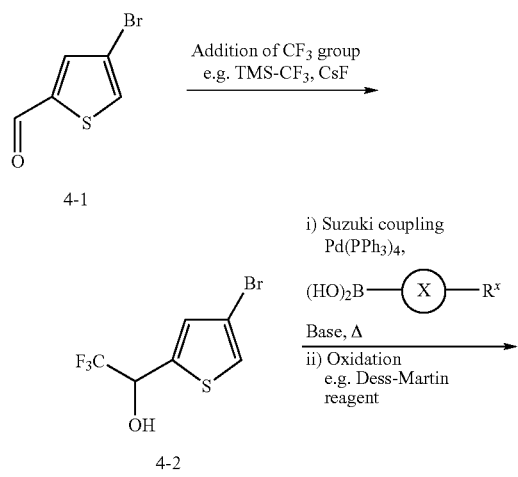

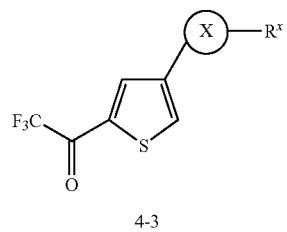

$R^x = (CH=CH)_c(CH_2)_b-Y-(CH_2)_a-Z$

Alternatively, 1,2,3-triazoles can be prepared utilizing 'click chemistry' as described by Prased Apukkuttan et al in *Org. Lett.* 2004, 6(23), 4223 and shown in scheme 5. Sonogashira cross-coupling of the 5-bromothiophene with trimethylsilylacetylene and subsequent deprotection liberated the unsubstituted acetylene 5-2. Treatment of this material with a mixture of a bromide, sodium azide and a mixture of copper powder and copper sulfate solution generates in situ an organic azide that can undergo a [3+2]cycloaddition reaction with the acetylene to generate the requisite HDAC inhibitor upon irradiation with microwaves.

Scheme 5 i) Sonogashira Rxt
   Pd(PPh$_3$)$_2$Cl$_2$, CuI
   TMS-CCH, Et$_3$N
ii) Deprotection, e.g.
    LiOH

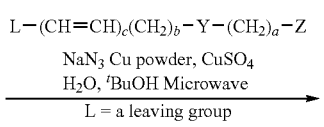

3-2

$L-(CH=CH)_c(CH_2)_b-Y-(CH_2)_a-Z$

NaN$_3$ Cu powder, CuSO$_4$
H$_2$O, $^t$BuOH Microwave
L = a leaving group 5-1

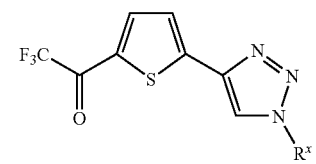

5-2

$R^x = (CH=CH)_c(CH_2)_b-Y-(CH_2)_a-Z$

Access to thiazoles can be accomplished using a cyclodehydration sequence as described in scheme 6. Activation of the carboxylic acid with reagents such as polymer supported carbodiimide allows coupling with an α-aminomethyl ketone to give the intermediate 6-1. Cyclisation of this material can be achieved by treatment with Lawesson's reagent and heating using a microwave irradiation.

Scheme 6

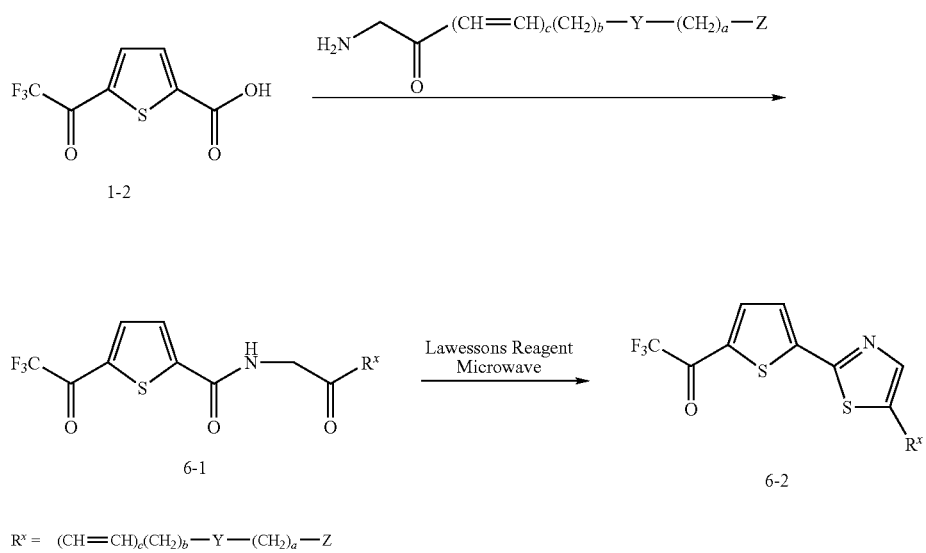

Similar methodology can be used in the thiazole series either by addition of a $CF_3$ group to an aldehyde 7-1 followed by oxidation of the subsequent intermediate 7-2 to yield the desired HDAC inhibitor 7-3 (Scheme 7). Alternatively, a procedure similar to those described above can be utilized whereby palladium cross-coupling is performed on the functionalised thiazole 7-5 prior to yield intermediate compounds 7-2 prior the final oxidation to compounds like 7-3.

Scheme 7

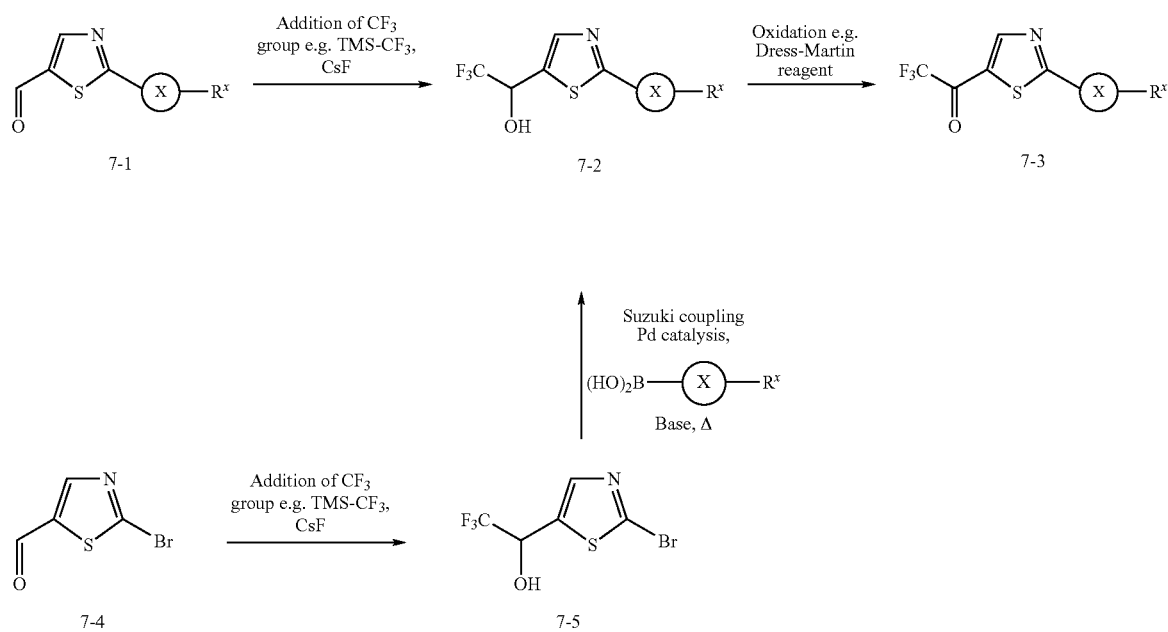

The exemplified compounds described herein were tested by the assays described below and were found to have an $IC_{50}$ value of less than 10 µM.

Preparation of HDACs 4+6 and Corresponding Assays

HDAC 4 Expression and Affinity Purification

The His-tagged HDAC 4, wild-type catalytic domain, was expressed in *E. coli* strain BL21 Star™ (DE3). The cells were grown at 37° C. in minimum medium supplemented with 1 g/l ($^{15}NH_4$)$SO_4$ and 5 g/l glucose, and 100 µM of $ZnCl_2$ to an optical density of 0.8 at 600 nm and induced with IPTG for 16 hr at 23° C. At 23° C. more than 800% of the protein was soluble.

Bacterial pellets were resuspended in 25 mM Hepes pH 7.5, 200 mM KCl, 0.5% NP-40, 20% glycerol 1 mM DTT and supplemented with Complete EDTA-free protease inhibitor. Subsequently bacterial pellets were lysed by microfluidizer, and centrifuged at 15000 rpm for 30 min.

The soluble fraction was diluted 1:1 with 25 mM Hepes pH 7.5, 200 mM KCl, 1 mM DTT and was loaded directly on His Trap HP 5 ml (Amersham Biosciences). The protein was eluted at 200 mM imidazole. The fractions with HDAC 4 were diluted 1:3 with 25 mM Hepes pH 7.5, 5% glycerol, 0.1% of NP40, 1 mM DTT. Then the solution was loaded on a Resource Q equilibrated with 25 mM Hepes pH 7.5, 10% glycerol, 50 mM KCl, 0.1% of NP40, 1 mM DTT. HDAC 4 was eluted with a salt gradient (0-250)mM of KCl. The product was fractionated by preparative SEC (G-75, Superdex 75 26/60 Amersham Biosciences) (25 mM Hepes pH 7.5, 150 mM KCl, 0.1% of β-octyl glucopiranoside, 1 mM DTT) to give the final product. Analytical SEC indicated that this product was monomeric. The protein was concentrated at ≈100 µM.

Flagged-HDAC 6 Expression and Affinity Purification

HEK 293 cells=6×10$^6$ cells/10 cm dish were transfected with 15 µg of plasmid DNA using Lipofectamine reagent (Invitrogen) according to the manufacturer's recommendations. After 24 hr, scrape cells in pre-cooled 1×PBS, centrifuge at 1500×g for 5 min at 4° C., washed twice with 1×PBS, count cells, collect cell pellet by centrifugation and freeze at −80° C.

Resuspend cell pellet in 1 ml of hypotonic lysis buffer (20 mM Hepes pH 7.9, 0.25 mM EDTA, 10% glycerol, 1 mM PMSF, Complete EDTA-free protease inhibitors cocktail from Boehringer) and incubated 15' on ice. Homogenize in Douncer 2 (25 strokes, B pestle), add to the homogenate 150 mM KCl and 0.5% NP40 (isotonic lysis buffer: ILB). Sonicate twice for 30 sec (output 5/6, duty cycle 90, timer constant), then incubate 60 min on a rotating wheel at 4° C. Centrifuge at 12000 rpm in SS34 rotor for 30 min at 4° C. and collect supernatant (soluble extract). Determine total protein concentration (BioRad reagent) and load 4, 8 and 16 µg of total protein on a 4-12% SDS-PAGE minigel together with 8-16 ng of reference protein. Establish flagged-HDAC6 concentration in the sample by Western blot analysis using an anti-FLAG alkaline phosphatase-conjugated monoclonal antibody (M2-AP, A9469, SIGMA)

Wash the anti-FLAG M2 affinity gel matrix (A2220, SIGMA) 3 times with 1×TBS and twice with ILB, centrifuge each time at 10000 rpm for 30 sec in an Eppendorf microfuge. Incubate slurry at RT for a few minutes before use. Use 10 µl of gel matrix for each 2 µg of flagged-HDAC6 in the soluble extract, mix gel matrix and soluble extract and incubate O/N on a rotating wheel at 4° C. Recover gel matrix by centrifugation and wash it once with ILB, twice with ILB containing 0.1% NP-40, and a further 2 times in elution buffer [50 mM Hepes pH 7.4, 5% glycerol, 0.01% Triton X-100, 100 mM KCl. Elute protein by adding to the gel matrix 10 volumes of elution buffer containing 100 µg/ml of 3×FLAG peptide (F4799, SIGMA) and incubation for 60 min on a rotating wheel at RT; recover eluted protein by centrifugation. Estimate flagged-HDAC6 concentration in the sample by anti-FLAG Western blot analysis (dilute eluted protein 30 folds with SDS-PAGE loading buffer and load 3, 10 and 30 µl, in parallel use 4, 8 and 16 ng of reference protein for quantification). Prepare 50 µl aliquots and snap freeze in liquid $N_2$ before storage at −80° C.

HDAC 4 Assay

Working Reagents

TSA Stock: TSA is provided as a 10 mM solution in 100% DMSO.

Assay buffer: 25 mM Tris/HCl pH8, 137 mM NaCl, 2.7 mM KCl, 1 mM $MgCl_2$, 0.1 mg/ml BSA Diluted substrate solution: tert-butyl {(1S)-1-{[(4-methyl-2-oxo-2H-chromen-7-yl)amino]carbonyl}-5-[(trifluoroacetyl)amino]pentyl}carbamate is diluted to 200 µM with Tris 1 mM pH 7.4 prior to each use. The final concentration in the assay is 20 µM.

Diluted developer solution: The commercial 20× developer concentrate (KI-105, BioMol Research Laboratories) is diluted 1:167 into Tris 1 mM pH7.4. 2 µM [final] TSA to this solution increases its ability to stop the reaction.

Enzyme working solution: Enzyme is diluted in 1.25× assay buffer prior to each use from a fresh aliquot of enzyme. The final concentration in the assay is 0.2 nM.

Experimental Design:

The reaction is performed in 96-well microplate in a final volume of 50 µl/well. Add 5 µl of DMSO/compound solution, add 40 µl of HDAC 4 enzyme in assay buffer and incubate 10' at RT. Start the reaction by adding 5 µl of the 200 µM substrate solution and incubate 1 hr at 37° C. Stop the reaction by adding 50 µl of developer/4 µM TSA solution and incubate 30 min at RT. Measure the fluorescence at ex.360 nM and em.460 nM.

HDAC 6 Assay

Working Reagents:

TSA stock: TSA is provided as a 10 mM stock solution in 100% DMSO.

Assay buffer: 20 mM Hepes pH 7.5, 137 mM NaCl, 2.7 mM KCl, 1 mM $MgCl_2$, 0.1 mg/ml BSA Diluted substrate solution: The 50 mM Fluor-de-Lys™ substrate (KI-104, BioMol Research Laboratories) is diluted to 150 µM with HDAC assay buffer prior to each use. The final concentration in the assay is 30 µM.

Diluted developer solution: The commercial 20× developer concentrate (KI-105, BioMol Research Laboratories) is diluted 1:167 into HDAC assay buffer. 2 µM [final] TSA to this solution increases its ability to stop the reaction.

HDAC 6 working solution: The HDAC 6 enzyme is diluted in assay buffer prior to each use from a fresh aliquot of enzyme. The final concentration in the assay is 1-2 nM.

Experimental Design:

The reaction is performed in 96-well microplate in a final volume of 50 μl/well. Add 5 μl of DMSO/compound solution and then 35 μl of HDAC 6 enzyme in assay buffer (or 3511 assay buffer in the negative controls) and incubate 10' at RT. Start the reaction by adding 10l of the 150 μM substrate solution and incubate for 1 hr at 37° C. Stop the reaction by adding 50 μl of developer/4 μM TSA solution and incubate 30 min at RT. Measure the fluorescence at ex.360 nM and em.460 nM.

Abbreviations Used Above are:

BSA (bovine serum albumin); DMSO (dimethyl sulfoxide); DTT (dithiothreitol); EDTA (ethylenediaminetetraacetic acid); em (emission); ex (exitation); Hepes ((N-(2-Hydroxyethyl)piperazine)-N'-2-ethanesulfonic acid)); ILB (isotonic lysis buffer);

IPTG (Isopropyl-beta-D-thiogalactopyranoside); NP40 (Nonidet P40); PBS (Phosphate buffered saline); O/N overnight; PMSF (phenylmethylsulphonyl fluoride);

RT (room temperature); SEC (size exclusion chromatography); TBS (Tris buffered saline); Tris-HCl (Tris Hydroxymethylaminoethane); and TSA (Trichostatin A).

The following Examples illustrate the present invention.

EXAMPLE 1

2,2,2-Trifluoro-1-[5-(3-{[(4-fluorobenzyl)sulfonyl]methyl}-1,2,4-oxadiazol-5-yl)-2-thienyl]ethanone. (A2)

Step 1: 5-(Trifluoroacetyl)thiophene-2-carboxylic acid (A1)

Ethyl 5-(trifluoroacetyl)thiophene-2-carboxylate was hydrolysed with LiOH (2.1 eq.) in MeOH/H$_2$O (1:1) at RT for 48 h. The mixture was concentrated under reduced pressure and extracted with EtOAc. The organic phase was washed with brine, dried (Na$_2$SO$_4$) and concentrated under reduced pressure to give the title compound as white solid. MS (ES) C$_7$H$_3$F$_3$O$_3$S requires: 224, found: 243 (M+H$_2$O+H)$^+$.

Step 2: 2,2,2-Trifluoro-1-[5-(3-{[(4-fluorobenzyl)sulfonyl]methyl}-1,2,4-oxadiazol-5-yl)-2-thienyl]ethanone (A2)

The above acid (A1) was dissolved in DMF and a solution of CDI (1.1 eq) in DMF was added. The mixture was stirred at RT for 30 min, then 2-[(4-fluorobenzyl)sulfonyl]-N-hydroxyethanimidamide (1.1 eq.) in DMF was added and the mixture stirred at RT overnight. The resulting intermediate (1Z)-2-[(4-fluorobenzyl)sulfonyl]-N'-({[5-(trifluoroacetyl)-2-thienyl]carbonyl}oxy)ethanimidamide (MS (ES) C$_{16}$H$_{12}$F$_4$N$_2$O$_5$S$_2$ requires: 452, found: 471 (M+H$_2$O+H)$^+$) was not isolated, instead CDI (1.1 eq) in DMF was added and the mixture was heated in a microwave oven (sealed tube, 140° C., 2 min). The product was isolated by preparative RP-HPLC, using H$_2$O (0.1% TFA) and MeCN (0.1% TFA) as eluents (column: C18). The pooled product fractions were evaporated to afford the title compound. $^1$H NMR (300 MHz, CD$_3$CN): δ8.1-8.07 (2H, m), 7.91 (0.1H, d, J=4 Hz, hydrate form), 7.58-7.49 (2H, m), 7.41 (0.1H, d, J=4 Hz, hydrate form), 7.25-7.12 (2H, m), 4.57 (2H, s), 4.54 (2H, s), 4.48 (0.2H, s, hydrate form). $^{19}$F NMR decoupled (282 MHz, CD$_3$CN): δ–73.78 (keto form), –85.45 (hydrate form), –114.51. MS (ES) C$_{16}$H$_{10}$F$_4$N$_2$O$_4$S$_2$ requires: 434, found: 453 (M+H$_2$O+H)$^+$, MS (ES–) 433 (M–H+e)$^-$.

EXAMPLE 2

1-{5-[5-(2-ethoxyphenyl)-1,3,4-oxadiazol-2-yl]-2-thienyl}-2,2,2-trifluoroethanone (B1)

To a solution of the carboxylic acid (A1) in DCM was added to PS-CDI (1.7 eq., loading 1.30 mmol/g), and the suspension stirred at RT for 30 min. 2-Ethoxybenzohydrazide (1.3 eq.) dissolved in DCM/DMF was added, and the resulting suspension was stirred at RT overnight. The suspension was filtered and the filtrate evaporated. The crude N'-(2-ethoxybenzoyl)-5-(trifluoroacetyl)thiophene-2-carbohydrazide (MS (ES) C$_{16}$H$_{13}$F$_3$N$_2$O$_4$S requires: 386, found: 427 (M+H$_2$0+Na)$^+$ and 385 (M–H+e)$^-$) was used as such, without any purification. It was dissolved in excess thionyl chloride and the solution was heated in a microwave oven (sealed tube, 100° C., 5 min) and the thionyl chloride was evaporated. The desired product was isolated by preparative RP-HPLC, using H$_2$O (0.1% TFA) and MeCN (0.1% TFA) as eluents (column: C18). The pooled product fractions were evaporated to afford the title compound. $^1$H NMR (300 MHz, CD$_3$CN): δ8.1-8.08 (1H, m), 8.06-8.01 (1H, m), 7.95-7.90 (1H, m), 7.63-7.56 (1H, m), 7.23-7.17 (1H, m), 7.16-7.09 (1H, m), 4.23 (2H, q, J=7 Hz), 1.48 (3H, t, J=7 Hz). $^{19}$F NMR (282 MHz, CD$_3$CN); δ –74.25 (keto form), –86.14 (hydrate form). MS (ES) C$_{16}$H$_{11}$F$_3$N$_2$O$_3$S requires: 368, found: 369 (M+H)$^+$ and 387 (M+H$_2$O+H)$^+$.

EXAMPLE 3

2,2,2-Trifluoro-1-{5-[4-methylsulfinyl)phenyl]-2-thienyl}ethanone (C3)

Step 1: 1-(5-Bromo-2-thienyl)-2,2,2-trifluoroethanol (C1)

To a stirred solution of 5-bromothiophene-2-carboxaldehyde (1.0 equiv) in dry glyme at RT, was added CsF (0.1 eq.) followed by dropwise addition of TMSCF$_3$ (1.2 eq.). The reaction mixture was stirred for 2 hr, then quenched by adding 3N HCl and stirred for 30 min. The organics were extracted with DCM and the organic extracts were combined and washed with brine and dried (Na$_2$SO$_4$). Evaporation of the solvent gave the crude product which was purified by flash column chromatography on silica using 1-10% EtOAc/Petroleum ether to yield the desired compound as an oil. $^1$H NMR (300 MHz, CDCl$_3$, 300K) δ 7.00 (1H, d, J=3.7 Hz), 6.94 (1H, d, J=3.7 Hz), 5.18 (1H, q, J=6.2 Hz), 3.61 (1H, broad s).

Step 2: 1-(5-Bromo-2-thienyl)-2,2,2-trifluoroethanone (C2)

A solution of the alcohol (C1) in DCM at RT was added Dess-Martin reagent (1.0 eq) and the reaction mixture was stirred 3 hr and then quenched by pouring into saturated aqueous NaHCO$_3$ solution containing 7 fold excess of Na$_2$S$_2$O$_3$. The mixture is stirred for 30 min and then the layers were separated and the organic layer was washed with water, brine and dried (Na$_2$SO$_4$). Evaporation of the solvent gave the crude product which was purified flash column chromatography using 1-10% EtOAc/Petroleum ether to yield the desired compound as an oil. $^1$H NMR (300 MHz, CDCl$_3$, 300K) δ 7.70 (1H, m), 7.21 (1H, d, J=4.2 Hz).

Step 3: 2,2,2-Trifluoro-1-{5-[4-methylsulfinyl)phenyl]-2-thienyl}ethanone (C3)

A mixture of the 5-bromothiophene (C2) (1.0 eq) and [4-(methylsulfinyl)phenyl]boronic acid (1.3 eq) in DMF (1.0M), together with 2N $Na_2CO_3$ aqueous solution (2.0 eq) was degassed with a stream of Ar for 10 min. $Pd(PPh_3)_4$ (0.05 eq) was added and the reaction heated overnight at 90° C. The reaction mixture was concentrated under reduced pressure and DCM was added. The organic phase was washed with 1N NaOH, brine, dried ($Na_2SO_4$), and concentrated under reduced pressure. The crude material was purified by preparative RP-HPLC, using $H_2O$ (0.1% TFA) and MeCN (0.1% TFA) as eluents (column: C18) and the desired fractions were freeze dried to yield the product (C3). $^1$H NMR (400 MHz, $CD_3CN$, 300k) δ 7.91 (1H, m), 7.78 (2H, d, J=8.8 Hz), 7.47 (2H, d, J=8.8 Hz), 6.71 (1H, d, J=4.6 Hz), 2.72 (3H, s). MS (ES) $C_{13}H_9F_3O_2S_2$ requires: 318, found: 319 (M+H$^+$).

EXAMPLE 4

1-[5-(1-Benzyl-1H-1,2,3-triazol-4-yl)-2-thienyl]-2,2,2-trifluoroethanone (D3)

Step 1: 2,2,2-Trifluoro-1-{5-[(trimethylsilyl)ethynyl]-2-thienyl}ethanone (D1)

A mixture of 5-bromo-thiophene Example 3, C2 (1.0 eq), $Pd(PPh_3)_2Cl_2$ (0.025 eq), CuI (0.05 eq) and $Et_3N$ (28.7 eq) in THF (0.25 M) was degassed with a stream of Ar for 30 min. Trimethylsilylacetylene (1.5 eq) was added and the mixture was stirred O/N at RT. Evaporation of the solvent gave a residue which was purified by flash column chromatography on silica using 0-5% EtOAc/Petroleum ether to yield the desired compound as a yellow oil. $^1$H NMR (300 MHz, $CDCl_3$, 300K) δ 7.83-7.78 (1H, m), 7.25 (1H, bs), 0.28 (9H, s).

Step 2: 1-(5-Ethynyl-2-thienyl)-2,2,2-trifluoroethanone (D2)

To a stirred solution of D1 (1.0 eq) in THF (0.1 M) at RT was added a solution of LiOH (2.0 eq) in $H_2O$ (0.1 M) and the reaction mixture was stirred for 1 hr, then quenched by adding 6M HCl solution until pH=2. The organic solvent was evaporated and the product was extracted by DCM. Organic layers were washed with brine and dried ($Na_2SO_4$). Evaporation of the solvent under reduced pressure gave the crude product which was purified by flash column chromatography using Pentane to yield the desired compound as a brown oil. $^1$H NMR (300 MHz, $CDCl_3$, 300K) δ 7.85-7.80 (1H, m), 7.32 (1H, d, J=4.2 Hz), 3.66 (1H, s).

Step 3: 1-[5-(1-Benzyl-1H-1,2,3-triazol-4-yl)-2-thienyl]-2,2,2-trifluoroethanone (D3)

Benzyl bromide (1.0 eq), D2 (1.05 eq) and $NaN_3$ (1.05 eq) were suspended in a 1:1 mixture of $H_2O$ and t-BuOH (0.1M) in a 10-mL glass vial equipped with a small magnetic stirring bar. To this was added Cu powder (0.8 eq) and $CuSO_4$ solution (1.0M, 0.2 eq) and the vial was tightly sealed with an aluminum/Teflon crimp top. The mixture was then irradiated for 10 min at 125° C., using an irradiation power of 100 W. After completion of the reaction, the vial was cooled to 50° C. with air jet cooling before it was opened. It was then diluted with $H_2O$ and precipitated product was collected by filtration, and washed with cold $H_2O$, followed by 0.25M HCl and finally with Petroleum ether to furnish a crude material which was purified by preparative RP-HPLC, using $H_2O$ (+0.1% TFA) and MeCN (+0.1% TFA) as eluents (column: C18) and the desired fractions were freeze dried to yield the product (D3). $^1$H NMR (400 MHz, DMSO, 300K). δ 8.92 (1H, s), 8.16-8.12 (1H, m), 7.73 (1H, d, J=4.4 Hz), 7.44-7.33 (5H, m), 5.70 (2H, s). MS (ES) $C_{15}H_{10}F_3N_3OS$ requires: 337, found: 338 (M+H$^+$) and 356 (M+$H_2O$+H)$^+$.

EXAMPLE 5

2,2,2-Trifluoro-1-(4-quinoxalin-6-yl-2-thienyl)ethanone (E4)

Step 1: 1-(4-Bromo-2-thienyl)-2,2,2-trifluoroethanol (E1)

To a stirred solution of 4-bromothiophene-2-carboxaldehyde (1.0 eq.) in dry glyme at RT, was added CsF (0.1 eq.) followed by dropwise addition of $TMSCF_3$ (1.2 eq.). The reaction mixture was stirred for 2 hr, then quenched by adding 3N HCl and stirred for 30 min. The organics were extracted with DCM (3×) and the organic extracts were combined and washed with brine and dried ($Na_2SO_4$). Evaporation of the solvent gave the crude product which was purified by flash column chromatography on silica using 10-90% EtOAc/Petroleum ether to yield the desired compound (A1) as oil. $^1$H NMR (300 MHz, $CDCl_3$, 300K) δ 7.27 (1H, s), 7.09 (1H, s), 5.22 (1H, q, J=6.2 Hz), 4.00 (1H, broad s).

Step 2: 6-(5,5-Dimethyl-1,3,2-dioxaborinan-2-yl)quinoxaline (E2)

A mixture of 6-bromoquinoxaline (1.0 eq.), bis-(neopentylglycolato)diborane (1.1 eq.), KOAc (3.0 eq.) and Pd(dppf)$Cl_2$ (0.05 eq.) in 1,4-dioxane was degassed with a stream of Ar for 10 minutes and then heated at 110° C. for 4 hrs. The reaction mixture was concentrated and the residue used in the next step without further purification. MS (ES) $C_{13}H_5BN_2O_2$ requires: 242, found: 175 (M-[$C_5H_{10}$]+H$^+$).

Step 3: 2,2,2-Trifluoro-1-(4-quinoxalin-6-yl-2-thienyl)ethanol (E3)

A mixture of the alcohol (E1) (1.0 eq.) and the crude boronic ester (E2) (1.3 eq.) in DMF (1.0M), together with 2N $Na_2CO_3$ aqueous solution (2.0 eq.) was degassed with a stream of Ar for 10 min. $Pd(PPh_3)_4$ (0.05 eq) was added and the reaction heated overnight at 90° C. The reaction mixture was concentrated under reduced pressure and the residue was purified by flash column chromatography on silica using 500% EtOAc/Petroleum ether to yield the desired compound as a power. $^1$H NMR (400 MHz, $CDCl_3$, 300K) δ 8.81 (2H, m), 8.20 (1H, d, J=2.0 Hz), 8.10 (1H, d, J=8.8 Hz), 7.98 (1H, dd, J=8.8, 2.0 Hz), 7.68 (1H, s), 7.61 (1H, s), 5.38 (1H, q, J=6.4 Hz). MS (ES) $C_{14}H_9F_3N_2OS$ requires: 310, found: 311 (M+H$^+$).

Step 4: 2,2,2-Trifluoro-1-(4-quinoxalin-6-yl-2-thienyl)ethanone (E4)

To a solution of the alcohol (E3) in DCM at RT was added Dess-Martin reagent (1.0 eq.) and the reaction mixture was stirred 3 hr and then quenched by adding a sat. aq. $Na_2S_2O_3$ solution. The mixture is stirred for 30 min and then the layers were separated and the organic layer was washed with water, brine and dried ($Na_2SO_4$). Evaporation of the solvent under reduced pressure gave a residue which was purified by flash column chromatography on silica using 50% EtOAc/Petroleum ether to yield the desired compound as a powder (E3). $^1$H NMR (300 MHz, DMSO, 300K) δ 9.06 (1H, s), 8.98 (2H, m), 8.74 (1H, s), 8.62 (1H, s), 8.38 (1H, d, J=8.7 Hz), 8.18 (1H, d, J=8.7 Hz). MS (ES) $C_{14}H_7F_3N_2OS$ requires: 308, found: 309 (M+H$^+$) and 327 (M+H$_2$O+H)$^+$.

EXAMPLE 6

2,2,2-Trifluoro-1-{5-[4-(methylthio)phenyl]-2-thienyl}ethanone (F1)

1-(5-Bromo-4-thienyl)-1,2,2-trifluoroethanol (C1) in DUE added to Polymer-Bound Triphenylphosphine Pd(0) (0.5% eq) followed by 4-(methylthio)phenylboronic acid (1.3 eq)) in EtOH and K$_2$CO$_3$ (1.5 eq) in water and the mixture was stirred at 75° C. for 24 h. The suspension was filtered and the filtrate was purified by reverse phase HPLC as described for Example 3. MS (ES) $C_{13}H_9F_3OS_2$ requires: 302, found: 303 (M+H$^+$).

EXAMPLE 7

2,2,2-Trifluoro-1-{5-[5-phenyl-1,3-thiazol-2-yl]-2-thienyl}ethanone (G2)

Step 1: N-(2-Oxo-2-phenylethyl)-5-(fluoroacetyl)thiophene-2-carboxamide (G1)

To a solution of Example 1, A1 in DCM was added Pol-supported carbodiimide (2 eq) and the suspension was stirred at RT for 30 min. A solution of 2-aminoacetophenone HCl (1.1 eq) and Et$_3$N (1.1 eq) in DCM was added and the resulting suspension was stirred at RT overnight. The resin was filtered, washed with DCM, and the filtrate was evaporated at reduced pressure. Purification by flash chromatography on silica gel eluting with DCM gave the title compound as a solid.
$^1$H NMR (300 MHz, CD$_3$CN): δ 8.05-8.01 (3H, m), 7.80-7.75 (1H, m), 7.70-7.52 (4H, m), 4.85 (2H, d, J=5.5 Hz). MS (ES) $C_{15}H_{10}F_3NO_3S$ requires: 341, found: 342 (M+H$^+$) and 360 (M+H$_2$O+H)$^+$.

Step 2: 2,2,2-Trifluoro-1-{5-[5-phenyl-1,3-thiazol-2-yl]-2-thienyl}ethanone (G2)

A mixture of G1 and Lawesson's reagent (4 eq) in toluene was placed in a sealed tube and heated in a microwave oven at 100° C. for 10 sec. The mixture was filtered through silica gel, eluting with DCM. The desired compound was isolated from the filtrate by flash chromatography on silica gel eluting with a mixture of petroleum ether and ethyl acetate to yield the desired compound as a yellow solid. $^1$H NMR (300 MHz CDCl$_3$): δ8.03 (1H, s), 7.91-3.88 (1H, m), 7.62-7.54 (3H, m), 7.48-7.39 (3H, m). MS (ES) $C_{15}H_8F_3NOS_2$ requires: 339, found: 340 (M+H$^+$), 358 (M+H$_2$O+H)$^+$ and 338 (M–H)$^-$.

EXAMPLE 8

2,2,2-Trifluoro-1-(2-phenyl-1,3-thiazol-5-yl)ethanone (H2)

Step 1: 2,2,2-Trifluoro-1-(2-phenyl-1,3-thiazol-5-yl)ethanone (H1)

A solution (0.15 M) of 2-phenyl-1,3-thiazole-5-carbaldehyde (1.0 eq.) and CsF (0.2 eq.) in DME was treated with CF$_3$SiMe$_3$ (1.5 eq.) and then stiffed for 3 h at RT. The reaction mixture was quenched by adding 1N HCl and stirred for 30 min. The mixture was diluted with EtOAc, the organic phase was separated, washed with sat. aq. NaHCO$_3$ solution and dried (Na$_2$SO$_4$). Evaporation of the solvent under reduced pressure afforded the product as an yellow oil. MS (ES$^+$) $C_{11}H_8F_3NOS$ requires: 259, found: 260

Step 2: 2,2,2-Trifluoro-1-(2-phenyl-1,3-thiazol-5-yl)ethanone (H2)

A solution of H1 in DCM (0.4 M) was treated with Dess-Martin-Periodinane (3.0 eq.) and stirred for 3 h at RT. Aq. sodium thiosulfate solution was added and the aqueous phase was extracted with DCM. The combined organic extracts were dried (Na$_2$SO$_4$) and solvents were removed under reduced pressure. The crude was purified by RP-HPLC (Waters SYMMETRY C18, 7 micron, 19×300 mm; flow: 20 mL/min; Gradient: A: H$_2$O (+0.1% TFA); B: MeCN (+0.1% TFA); 60% A linear to 10% A in 14 min) to afford the title compound as a solid after freeze drying the desired fractions. $^1$H NMR (300 MHz, CDCl$_3$, 300K) δ 7.59-7.47 (3H, m), 8.07-8.03 (2H, m), 8.60 (1H, s). MS (ES$^+$) $C_{11}H_6F_3NOS$ requires: 257, found: 258 (M+H)$^+$ and 276 (M+H+H$_2$0)$^+$.

EXAMPLE 9

2,2,2-Trifluoro-1-[2-(2-naphthyl)-1,3-thiazol-5-yl]ethanone (I3)

Step 1: 1-(2-Bromo-1,3-thiazol-5-yl)-2,2,2-trifluoroethanol (I1)

A solution (0.52 M) of 2-bromo-5-formylthiazole (1.0 eq.) and CsF (0.2 eq.) in DME was treated with CF$_3$SiMe$_3$ (2.0 eq.) and then stirred for 2 h at RT. The reaction mixture was quenched by adding water and stirred for 15 min. Then, it was diluted with EtOAc and the organic phase was separated. The aqueous phase was extracted twice with EtOAc. The combined organic phase was dried (Na$_2$SO$_4$) and solvents were removed under reduced pressure. The residue was purified by flash chromatography on silica gel eluting with 5-25% EtOAc/petroleum ether to afford the title compound as a yellow solid. $^1$H NMR (300 MHz, CDCl$_3$, 300K) δ 4.04 (1H, d, J=5.9 Hz), 5.32 (1H, dq, J=5.9 Hz, J=5.9 Hz), 7.59 (1H, s). MS (ES$^+$) $C_5H_3BrF_3NOS$ requires: 261/263, found: 262/264 (M+H)$^+$.

Step 2: 2,2,2-Trifluoro-1-[2-(2-naphthyl)-1,3-thiazol-5-yl]ethanol (I2)

A solution the bromide I1 (1.0 eq.), naphthalene-2-boronic acid (1.5 eq.), K$_2$CO$_3$ (1.5 eq.), triphenylphosphine (polymer bound 3 mmol/g, 1.0 eq.) and Pd(OAc)$_2$ (0.1 eq.) in DME/water/EtOH (4/1/1) was stirred 3 days at 70° C. under argon. After cooling, 1 N NaOH was added and the solution was washed with EtOAc through an Isolute HM-N column. The solvents were removed under reduced pressure to yield the crude material which was used in the next step without further purification. MS (ES$^+$) $C_{15}H_{10}F_3NOS$ requires: 309, found: 310 (M+H)$^+$.

Step 3: 2,2,2-Trifluoro-1-[2-(2-naphthyl)-1,3-thiazol-5-yl]ethanone (I3)

A solution of the crude product I2 in DCM was treated with Dess-Martin Periodinane (3.0 eq.) and stirred for 3 h at RT. Aq. sodium thiosulfate was added and the aqueous phase was extracted with DCM. The combined organic phase was dried (Na$_2$SO$_4$) and solvents were removed under reduced pressure. The crude was purified by RP-HPLC (Waters SYMMETRY C18, 7 micron, 19×300 mm; flow: 20 mL/min; Gradient: A: H$_2$O (+0.1% TFA); B: MeCN (+0.1% TFA); 60% A linear to 10% A in 14 min) to afford the title compound as a solid after freeze drying the desired fractions. $^1$H NMR (300 MHz, DMSO-d$_6$, 300K) δ 7.69-7.50 (3H, m), 8.27-7.92 (4H, m), 8.55 (1H, s). MS (ES$^+$) C$_{15}$H$_8$F$_3$NOS requires: 307, found: 308 (M+H)$^+$ and 326 (M+H+H$_2$O)$^+$.

EXAMPLE 10

N-(4-Fluorobenzyl)-5-(trifluoroacetyl)thiophene-2-carboxamide (J2)

Step 1: (4-[5-(trifluoroacetyl)-2-thienyl]benzoic acid) (J1)

The titled compound was prepared from 1-(5-bromo-2-thienyl)-2,2,2-trifluoroethanone (C2) (1.0 eq) and the corresponding 4-carboxyphenylboronic acid (1.3 eq) in DMF (1.0M) following the general procedure for Suzuki cross-coupling described in example 3 step 1. After completion of the reaction the solution mixture was concentrated under reduced pressure and 1N HCl solution was added. The resulting precipitate formed was washed several times with DCM and used in the next coupling reaction without further purification. $^1$H NMR (400 MHz, DMSO, 300K) δ 13.14 (1H, broad s), 8.18 (1H, broad s), 8.06-8.00 (4H, m), 7.95 (1H, d, J=4.2 Hz). MS (ES) C$_{13}$H$_7$F$_3$O$_3$S requires: 300, found: 301 (M+H$^+$).

Step 2: N-(4-fluorobenzyl)-5-(trifluoroacetyl)thiophene-2-carboxamide (J2)

To a stirred solution of the carboxylic acid (J1) (1.0 eq.) in DMF a solution of HOBt (1.5 eq.) and EDCl (1.5 eq.) in DMF was added and the mixture was stirred for 1 hour. 4-Fluorobenzylamine (1.5 eq) was added and the reaction mixture was stirred at RT for 16 hours. The resulting crude was purified by RP-HPLC and the desired fractions were freeze dried to yield the product (J2) as a powder. $^1$H NMR (400 MHz, DMSO, 300K) δ 9.19 (1H, broad t, J=5.8 Hz), 8.17 (1H, broad s), 8.00 (4H, s), 7.94 (1H, d, J=4.4 Hz), 7.37 (2H, dd, J=8.6, 5.7 Hz), 7.16 (2H, t, J=8.6 Hz), 4.48 (2H, d, J=5.8 Hz). MS (ES) C$_{20}$H$_{13}$F$_4$NO$_2$S requires: 407, found: 408 (M+H$^+$).

The following examples were prepared according to the procedures described above.

| Ex | Name | Procedure according to Example | MWt | (M + H)$^+$ | (M + H$_2$O + H)$^+$ | (M + H$_2$O + Na + H)$^+$ | (M − H)$^−$ |
|---|---|---|---|---|---|---|---|
| 11 | 2,2,2-Trifluoro-1-(5-{3-[(methylsulfonyl)methyl]-1,2,4-oxadiazol-5-yl}-2-thienyl)ethanone | 1 | 340 | 341 | | | 339 |
| 12 | 2,2,2-Trifluoro-1-(5-{3-[(propylsulfonyl)methyl]-1,2,4-oxadiazol-5-yl}-2-thienyl)ethanone | 1 | 368 | 369 | 387 | | 367 |
| 13 | 2,2,2-Trifluoro-1-(5-{3-[(2-thienylsulfonyl)methyl]-1,2,4-oxadiazol-5-yl}-2-thienyl)ethanone | 1 | 408 | 409 | 427 | | |
| 14 | 1-[5-(3-{4-[(2,4-Dichlorobenzyl)oxy]phenyl}-1,2,4-oxadiazol-5-yl)-2-thienyl]-2,2,2-trifluoroethanone | 1 | 499 | | 517 | | 497 |
| 15 | 1-{5-[3-(4-{[3-Chloro-5-(trifluoromethyl)-2-pyridinyl]methoxy}benzyl)-1,2,4-oxadiazol-5-yl]-2-thienyl}-2,2,2-trifluoroethanone | 1 | 547 | 548 | 566 | | 546; 564 (hydrate) |
| 16 | 1-(5-{3-[3,5-bis(Trifluoromethyl)benzyl]-1,2,4-oxadiazol-5-yl}-2-thienyl)-2,2,2-trifluoroethanone | 1 | 474 | | 493 | | 473 |
| 17 | 1-{5-[3-(2-Chloro-4-fluorobenzyl)-1,2,4-oxadiazol-5-yl]-2-thienyl}-2,2,2-trifluoroethanone | 1 | 390 | 391 | 409 | | 389 |
| 18 | 2,2,2-Trifluoro-1-(5-{3-[3-(trifluoromethyl)phenyl]-1,2,4-oxadiazol-5-yl}-2-thienyl)ethanone | 1 | 392 | | 411 | | 391 |
| 19 | 2,2,2-Trifluoro-1-(5-{3-[4-(trifluoromethoxy)phenyl]-1,2,4-oxadiazol-5-yl}-2-thienyl)ethanone | 1 | 408 | | 427 | | 407 |

| Ex | Name | Procedure according to Example | MWt | (M + H)+ | (M + H₂O + H)+ | (M + H₂O + Na + H)+ | (M − H)− |
|---|---|---|---|---|---|---|---|
| 20 | 2,2,2-Trifluoro-1-{5-[3-(4-fluorophenyl)-1,2,4-oxadiazol-5-yl]-2-thienyl}ethanone | 1 | 342 | | 361 | | 341 |
| 21 | 1-{5-[3-(3-{[(4-Chlorophenyl)sulfonyl]methyl}phenyl)-1,2,4-oxadiazol-5-yl]-2-thienyl}-2,2,2-trifluoroethanone | 1 | 512 | | 531 | | 511 |
| 22 | 3-({5-[5-(Trifluoroacetyl)-2-thienyl]-1,2,4-oxadiazol-3-yl}methyl)-1,3-benzoxazol-2(3H)-one | 1 | 395 | | 414 | | 394; 412 (hydrate) |
| 23 | 4-({5-[5-(Trifluoroacetyl)-2-thienyl]-1,2,4-oxadiazol-3-yl}methyl)-2H-1,4-benzoxazin-3(4H)-one | 1 | 409 | 410 | 428 | | 408 |
| 24 | 1-(5-{3-[6-Chloro-4-(phenylsulfonyl)-3,4-dihydro-2H-1,4-benzoxazin-2-yl]-1,2,4-oxadiazol-5-yl}-2-thienyl)-2,2,2-trifluoroethanone | 1 | 555 | | 574 | | 554; 572 (hydrate) |
| 25 | 2,2,2-Trifluoro-1-[5-(3-{4-[(2-methyl-1,3-thiazol-4-yl)methoxy]phenyl}-1,2,4-oxadiazol-5-yl)-2-thienyl]ethanone | 1 | 451 | 452 | 470 | | 450 |
| 26 | 1-{5-[3-(2,4-Difluorophenyl)-1,2,4-oxadiazol-5-yl]-2-thienyl}-2,2,2-trifluoroethanone | 1 | 360 | 361 | 379 | | |
| 27 | 2,2,2-Trifluoro-1-{5-[3-(4-methoxyphenyl)-1,2,4-oxadiazol-5-yl]-2-thienyl}ethanone | 1 | 354 | | 373 | | 353 |
| 28 | 1-[5-(3-{4-[(4-Chlorophenyl)sulfonyl]-3,4-dihydro-2H-1,4-benzoxazin-2-yl}-1,2,4-oxadiazol-5-yl)-2-thienyl]-2,2,2-trifluoroethanone | 1 | 555 | | 574 | | 572 (hydrate) |
| 29 | 2,2,2-Trifluoro-1-{5-[3-(2-thienylmethyl)-1,2,4-oxadiazol-5-yl]-2-thienyl}ethanone | 1 | 344 | 345 | 363 | | 343 |
| 30 | N-(4-{5-[5-(2,2,2-Trifluoroacetyl)-2-thienyl]-1,2,4-oxadiazol-3-yl}phenyl)acetamide | 1 | 381 | 382 | | | 380 |
| 31 | 2,2,2-Trifluoro-1-[5-(3-{[4-(1,3,4-oxadiazol-2-yl)phenoxy]methyl}-1,2,4-oxadiazol-5-yl)-2-thienyl]ethanone | 1 | 422 | 423 | | | 421 |
| 32 | 2,2,2-Trifluoro-1-{5-[3-(3-methylphenyl)-1,2,4-oxadiazol-5-yl]-2-thienyl}ethanone | 1 | 338 | | 357 | | 337 |
| 33 | 1-{5-[3-(4-Bromo-1-methyl-1H-pyrazol-3-yl)-1,2,4-oxadiazol-5-yl]-2-thienyl}-2,2,2-trifluoroethanone | 1 | 407 | | 425 | | 423 (hydrate) |
| 34 | 2,2,2-Trifluoro-1-{5-[3-(3-fluoro-4-methylphenyl)-1,2,4- | 1 | 356 | | 375 | | 355 |

| Ex | Name | Procedure according to Example | MWt | (M + H)⁺ | (M + H₂O + H)⁺ | (M + H₂O + Na + H)⁺ | (M − H)⁻ |
|---|---|---|---|---|---|---|---|
| 35 | oxadiazol-5-yl]-2-thienyl}ethanone 2,2,2-Trifluoro-1-[5-(3-methyl-1,2,4-oxadiazol-5-yl)-2-thienyl]ethanone | 1 | 262 | 263 | 281 | | 261 |
| 36 | 2,2,2-Trifluoro-1-{5-[5-(3-methoxyphenyl)-1,3,4-oxadiazol-2-yl]-2-thienyl}ethanone | 2 | 354 | 355 | 373 | | |
| 37 | 2,2,2-Trifluoro-1-{5-[5-(4-fluorophenyl)-1,3,4-oxadiazol-2-yl]-2-thienyl}ethanone | 2 | 342 | 343 | | | 341 |
| 38 | 2,2,2-Trifluoro-1-{5-[5-(2-furyl)-1,3,4-oxadiazol-2-yl]-2-thienyl}ethanone | 2 | 314 | 315 | | | |
| 39 | 2,2,2-Trifluoro-1-{5-[5-(2-thienyl)-1,3,4-oxadiazol-2-yl]-2-thienyl}ethanone | 2 | 330 | 331 | | | |
| 40 | 2,2,2-Trifluoro-1-[5-(5-phenyl-1,3,4-oxadiazol-2-yl)-2-thienyl]ethanone | 2 | 324 | 325 | | | |
| 41 | 2,2,2-Trifluoro-1-{5-[5-(4-methylphenyl)-1,3,4-oxadiazol-2-yl]-2-thienyl}ethanone | 2 | 338 | 339 | | | |
| 42 | 1-{5-[5-(4-tert-Butylphenyl)-1,3,4-oxadiazol-2-yl]-2-thienyl}-2,2,2-trifluoroethanone | 2 | 380 | 381 | | | |
| 43 | 1-{5-[5-(1,3-Benzodioxol-5-yl)-1,3,4-oxadiazol-2-yl]-2-thienyl}-2,2,2-trifluoroethanone | 2 | 368 | 369 | | | |
| 44 | 1-{5-[5-(2,5-Dimethoxyphenyl)-1,3,4-oxadiazol-2-yl]-2-thienyl}-2,2,2-trifluoroethanone | 2 | 384 | 385 | 403 | | |
| 45 | 2,2,2-Trifluoro-1-{5-[5-(2-fluorophenyl)-1,3,4-oxadiazol-2-yl]-2-thienyl}ethanone | 2 | 342 | 343 | | | |
| 46 | 1-{5-[5-(2-Chlorophenyl)-1,3,4-oxadiazol-2-yl]-2-thienyl}-2,2,2-trifluoroethanone | 2 | 358 | 359 | 377 | | 357 |
| 47 | 1-{5-[5-(4-Chlorophenyl)-1,3,4-oxadiazol-2-yl]-2-thienyl}-2,2,2-trifluoroethanone | 2 | 358 | 359 | 377 | | 357 |
| 48 | 1-{5-[5-(2,4-Dichlorophenyl)-1,3,4-oxadiazol-2-yl]-2-thienyl}-2,2,2-trifluoroethanone | 2 | 393 | 393 | 411 | | 391 |
| 49 | 2,2,2-Trifluoro-1-[5-(3-phenyl-1,2,4-oxadiazol-5-yl)-2-thienyl]ethanone | 1 | 324 | | 343 | | |
| 50 | 2,2,2-Trifluoro-1-(5-pyridin-2-yl-2-thienyl)ethanone | 3 | 257 | 258 | | | |
| 51 | 2,2,2-Trifluoro-1-(5-quinoxalin-6-yl-2-thienyl)ethanone | 3 | 308 | 309 | | | |
| 52 | 2,2,2-Trifluoro-1-[5-(4-methoxyphenyl)-2-thienyl]ethanone | 3 | 286 | 287 | | | |

-continued

| Ex | Name | Procedure according to Example | MWt | (M + H)⁺ | (M + H₂O + H)⁺ | (M + H₂O + Na + H)⁺ | (M − H)⁻ |
|---|---|---|---|---|---|---|---|
| 53 | 2,2,2-Trifluoro-1-[5-(4-phenoxyphenyl)-2-thienyl]ethanone | 3 | 348 | 349 | | | |
| 54 | 2,2,2-Trifluoro-1-[5-(2-methoxyphenyl)-2-thienyl]ethanone | 3 | 286 | 287 | | | |
| 55 | 1-[5-(2,3-Dihydro-1,4-benzodioxin-6-yl)-2-thienyl]-2,2,2-trifluoroethanone | 3 | 314 | 315 | | | |
| 56 | 4-[5-(Trifluoroacetyl)-2-thienyl]benzonitrile | 3 | 281 | 282 | | | |
| 57 | 1-[5-(4-Acetylphenyl)-2-thienyl]-2,2,2-trifluoroethanone | 3 | 298 | 299 | | | |
| 58 | 2,2,2-Trifluoro-1-{5-[3-(piperidin-1-ylcarbonyl)phenyl]-2-thienyl}ethanone | 3 | 367 | 368 | | | |
| 59 | 2,2,2-Trifluoro-1-[5-(1H-indol-5-yl)-2-thienyl]ethanone | 3 | 295 | 296 | | | |
| 60 | 2,2,2-Trifluoro-1-{5-[3-(1H-pyrazol-1-yl)phenyl]-2-thienyl}ethanone | 3 | 322 | 323 | | | |
| 61 | 4-{3-[5-(Trifluoroacetyl)-2-thienyl]benzyl}morpholin-4-ium trifluoroacetate | 3 | 355 | 356 | 374 | | |
| 62 | 2,2,2-Trifluoro-1-[5-(3-methoxyphenyl)-2-thienyl]ethanone | 3 | 286 | 287 | | | |
| 63 | 3-[5-(Trifluoroacetyl)-2-thienyl]benzoic acid | 3 | 300 | 301 | | | |
| 64 | N,N-Dimethyl{4-[5-(trifluoroacetyl)-2-thienyl]phenyl}methanaminium trifluoroacetate | 3 | 313 | 314 | 332 | | |
| 65 | 2,2,2-Trifluoro-1-(5-quinolin-6-yl-2-thienyl)ethanone | 3 | 307 | 308 | 326 | | |
| 66 | 2,2,2-Trifluoro-1-{5-[1-(2-naphthylmethyl)-1H-1,2,3-triazol-4-yl]-2-thienyl}ethanone | 4 | 387 | 388 | 406 | | |
| 67 | 1-{5-[1-(Cyclohexylmethyl)-1H-1,2,3-triazol-4-yl]-2-thienyl}-2,2,2-trifluoroethanone | 4 | 343 | 344 | 362 | | |
| 68 | 2,2,2-trifluoro-1-{5-[3-(3-methylpyridin-2-yl)-1,2,4-oxadiazol-5-yl]-2-thienyl}ethanone | 1 | 339 | 340 | 358 | | |
| 69 | 2,2,2-trifluoro-1-[5-(3-pyridin-4-yl-1,2,4-oxadiazol-5-yl)-2-thienyl]ethanone | 1 | 325 | 326 | | | 324 |
| 70 | 2,2,2-trifluoro-1-[5-(3-pyridin-2-yl-1,2,4-oxadiazol-5-yl)-2-thienyl]ethanone | 1 | 325 | 326 | 344 | 366 | |
| 71 | 2,2,2-trifluoro-1-(5-{3-[(phenylsulfonyl)methyl]-1,2,4-oxadiazol-5-yl}-2-thienyl)ethanone | 1 | 402 | | 421 | 443 | 401 |
| 72 | 4-{5-[5-(trifluoroacetyl)-2-thienyl]-1,2,4-oxadiazol-3-yl}phenyl dimethylsulfamate | 1 | 447 | 448 | 466 | 488 | 446 |

-continued

| Ex | Name | Procedure according to Example | MWt | (M + H)⁺ | (M + H₂O + H)⁺ | (M + H₂O + Na + H)⁺ | (M − H)⁻ |
|---|---|---|---|---|---|---|---|
| 73 | 2,2,2-trifluoro-1-[5-(3-{[(4-fluorophenyl)sulfonyl]methyl}-1,2,4-oxadiazol-5-yl)-2-thienyl]ethanone | 1 | 420 | 421 | 439 | 461 | 419 |
| 74 | 2,2,2-trifluoro-1-[5-(3-pyrazin-2-yl-1,2,4-oxadiazol-5-yl)-2-thienyl]ethanone | 1 | 326 | 327 | 345 | 367 | |
| 75 | 2,2,2-trifluoro-1-{5-[3-(2-thienyl)-1,2,4-oxadiazol-5-yl]-2-thienyl}ethanone | 1 | 330 | | 349 | | 329 |
| 76 | 2,2,2-trifluoro-1-(5-{3-[6-(trifluoromethyl)pyridin-3-yl]-1,2,4-oxadiazol-5-yl}-2-thienyl)ethanone | 1 | 393 | 394 | 412 | | |
| 77 | 2,2,2-trifluoro-1-(5-{3-[4-(trifluoromethyl)phenyl]-1,2,4-oxadiazol-5-yl}-2-thienyl)ethanone | 1 | 392 | | 411 | | 391 |
| 78 | 2,2,2-trifluoro-1-[5-(3-pyridin-3-yl-1,2,4-oxadiazol-5-yl)-2-thienyl]ethanone | 1 | 325 | 326 | 344 | | |
| 79 | 2,2,2-trifluoro-1-{5-[3-(4-methylphenyl)-1,2,4-oxadiazol-5-yl]-2-thienyl}ethanone | 1 | 338 | 339 | 357 | 379 | |
| 80 | 2,2,2-trifluoro-1-{5-[3-(2-oxo-2-pyrrolidin-1-ylethyl)-1,2,4-oxadiazol-5-yl]-2-thienyl}ethanol | 1 | 359 | 360 | 378 | 400 | 358 |
| 81 | 4-{5-[5-(trifluoroacetyl)-2-thienyl]-1,2,4-oxadiazol-3-yl}benzaldehyde | 1 | 352 | 353 | 371 | | 351 |
| 82 | 2,2,2-trifluoro-1-(5-{3-[(isopropylsulfonyl)methyl]-1,2,4-oxadiazol-5-yl}-2-thienyl)ethanone | 1 | 368 | | 387 | 409 | 367 |
| 83 | 1-{5-[3-(2,3-dihydro-1,4-benzodioxin-2-yl)-1,2,4-oxadiazol-5-yl]-2-thienyl}-2,2,2-trifluoroethanone | 1 | 382 | | 401 | 423 | |
| 84 | 1-(5-{3-[(4-tert-butylphenoxy)methyl]-1,2,4-oxadiazol-5-yl}-2-thienyl)-2,2,2-trifluoroethanone | 1 | 410 | | 429 | 451 | |
| 85 | 1-[5-(3-{[(4-chlorophenyl)sulfonyl]methyl}-1,2,4-oxadiazol-5-yl)-2-thienyl]-2,2,2-trifluoroethanone | 1 | 436 | | 455 | 477 | 435 |
| 86 | 1-{5-[3-(2,4-dichlorophenyl)-1,2,4-oxadiazol-5-yl]-2-thienyl}-2,2,2-trifluoroethanone | 1 | 393 | | | 434 | |
| 87 | phenyl({5-[5-(trifluoroacetyl)-2-thienyl]-1,2,4-oxadiazol-3-yl}methyl)sulfoniumolate | 1 | 386 | | | 427 | |

| Ex | Name | Procedure according to Example | MWt | (M + H)⁺ | (M + H₂O + H)⁺ | (M + H₂O + Na + H)⁺ | (M − H)⁻ |
|---|---|---|---|---|---|---|---|
| 88 | N-(3,4-dichlorophenyl)-2-{5-[5-(trifluoroacetyl)-2-thienyl]-1,2,4-oxadiazol-3-yl}acetamide | 1 | 450 | | 469 | 492 | |
| 89 | 2-Morpholin-4-yl-5-[5-(trifluoroacetyl)-2-thienyl]pyridinium trifluoroacetate | 3 | 342 | 343 | 361 | | |
| 90 | Methyl 4-[5-(trifluoroacetyl)-2-thienyl]benzoate | 3 | 314 | 315 | 333 | | |
| 91 | 2,2,2-trifluoro-1-[5-(6-methoxypyridin-3-yl)-2-thienyl]ethanone | 3 | 287 | 288 | 306 | | |
| 92 | 2,2,2-trifluoro-1-(5-quinolin-8-yl-2-thienyl)ethanone | 3 | 307 | 308 | 326 | | |
| 93 | 2,2,2-trifluoro-1-(5-quinolin-3-yl-2-thienyl)ethanone | 3 | 307 | 308 | 326 | | |
| 94 | 1-{5-[3-(3,5-dimethyl-1H-pyrazol-1-yl)phenyl]-2-thienyl}-2,2,2-trifluoroethanone | 3 | 350 | 351 | 369 | | |
| 95 | 1-[5-(1-benzothien-7-yl)-2-thienyl]-2,2,2-trifluoroethanone | 3 | 312 | 313 | | | |
| 96 | 2,2,2-trifluoro-1-{5-[4-(1H-pyrazol-1-yl)phenyl]-2-thienyl}ethanone | 3 | 322 | 323 | 341 | | |
| 97 | N-Methyl-N-(quinoxalin-6-ylmethyl)-3-[5-(trifluoroacetyl)-2-thienyl]benzamide | 10 | 455 | 456 | 474 | | |
| 98 | 2,2,2-Trifluoro-1-[5-(4-nitrophenyl)-2-thienyl]ethanone | 3 | 301 | 302 | 320 | | |
| 99 | 2,2,2-Trifluoro-1-{5-[4-(trifluoromethyl)phenyl]-2-thienyl}ethanone | 3 | 324 | 325 | | | |
| 100 | 2,2,2-trifluoro-1-[5-(1H-pyrazol-3-yl)-2-thienyl]ethanone | 3 | 246 | 247 | 265 | | |
| 101 | 5-[5-(trifluoroacetyl)-2-thienyl]isoquinolinium trifluoroacetate | 3 | 307 | 308 | 326 | | |
| 102 | 2,2,2-trifluoro-1-(5-pyrimidin-5-yl-2-thienyl)ethanone | 3 | 258 | 259 | 277 | | |
| 103 | 1-[5-(1-benzothien-3-yl)-2-thienyl]-2,2,2-trifluoroethanone | 6 | 312 | 313 | | | |
| 104 | 2,2,2-trifluoro-1-[5-(4-isopropoxyphenyl)-2-thienyl]ethanone | 6 | 314 | 315 | | | |
| 105 | N-{4-[5-(2,2,2-trifluoroacetyl)-2-thienyl]phenyl}acetamide | 6 | 313 | 314 | | | 312 |
| 106 | 1-[5-(1,3-benzodioxol-5-yl)-2-thienyl]-2,2,2-trifluoroethanone | 6 | 300 | 301 | | | |
| 107 | N-{4-[5-(2,2,2-trifluoroacetyl)-2-thienyl]phenyl}methanesulfonamide | 6 | 349 | 350 | | | 348 |

-continued

| Ex | Name | Procedure according to Example | MWt | (M + H)+ | (M + H2O + H)+ | (M + H2O + Na + H)+ | (M − H)− |
|---|---|---|---|---|---|---|---|
| 108 | tert-butyl {3-[5-(trifluoroacetyl)-2-thienyl]phenyl}carbamate | 6 | 371 | | | | 370 |
| 109 | 2,2,2-Trifluoro-1-{5-[1-(4-methylbenzyl)-1H-1,2,3-triazol-4-yl]-2-thienyl}ethanone | 4 | 351 | 352 | 370 | | |
| 110 | 4-({4-[5-(Trifluoroacetyl)-2-thienyl]-1H-1,2,3-triazol-1-yl}methyl)benzonitrile | 4 | 362 | 363 | 381 | | |
| 111 | 2,2,2-Trifluoro-1-(5-{1-[4-(methylsulfonyl)benzyl]-1H-1,2,3-triazol-4-yl}-2-thienyl)ethanone | 4 | 415 | 416 | 434 | | |
| 112 | 2,2,2-Trifluoro-1-[5-(1-{2-[(phenylsulfonyl)methyl]benzyl}-1H-1,2,3-triazol-4-yl)-2-thienyl]ethanone | 4 | 491 | 492 | 514 | | |
| 113 | 1-{5-[1-(1,3-Benzothiazol-2-ylmethyl)-1H-1,2,3-triazol-4-yl]-2-thienyl}-2,2,2-trifluoroethanone | 4 | 394 | 395 | 413 | | |
| 114 | 1-{5-[1-(Cyclobutylmethyl)-1H-1,2,3-triazol-4-yl]-2-thienyl}-2,2,2-trifluoroethanone | 4 | 315 | 316 | 334 | | |
| 115 | 4-[5-(Trifluoroacetyl)-2-thienyl]benzoic acid | 10 | 300 | 301 | 319 | | |
| 116 | N-(4-Fluorobenzyl)-3-[5-(trifluoroacetyl)-2-thienyl]benzamide | 10 | 407 | 408 | 426 | | |
| 117 | N-Methyl-N-(quinoxalin-6-ylmethyl)-4-[5-(trifluoroacetyl)-2-thienyl]benzamide | 10 | 455 | 456 | 474 | | |
| 118 | (2E)-3-{4-[5-(Trifluoroacetyl)-2-thienyl]phenyl}acrylic acid | 3 | 326 | 327 | 345 | | |
| 119 | (2E)-3-{3-[5-(Trifluoroacetyl)-2-thienyl]phenyl}acrylic acid | 3 | 326 | 327 | 345 | | |
| 120 | 1-[5-(4-Benzoylphenyl)-2-thienyl]-2,2,2-trifluoroethanone | 3 | 360 | 361 | 379 | | |
| 121 | 2,2,2-trifluoro-1-(5-pyridin-3-yl-2-thienyl)ethanone | 3 | 257 | 258 | 276 | | |
| 122 | 2,2,2-trifluoro-1-{5-[2-(1H-pyrazol-1-yl)phenyl]-2-thienyl}ethanone | 3 | 322 | 323 | 341 | | |
| 123 | (2E)—N-Methyl-N-(quinoxalin-6-ylmethyl)-3-{4-[5-(trifluoroacetyl)-2-thienyl]phenyl}acrylamide | 10 | 481 | 482 | 500 | | |

| Ex | Name | Procedure according to Example | MWt | (M + H)+ | (M + H2O + H)+ | (M + H2O + Na + H)+ | (M − H)− |
|---|---|---|---|---|---|---|---|
| 124 | (2E)-N-(4-Fluorobenzyl)-3-{4-[5-(trifluoroacetyl)-2-thienyl]phenyl}acrylamide | 10 | 433 | 434 | 452 | | |
| 125 | (2E)-N-Methyl-N-(quinoxalin-6-ylmethyl)-3-{3-[5-(trifluoroacetyl)-2-thienyl]phenyl}acrylamide | 10 | 481 | 482 | 500 | | |
| 126 | (2E)-N-(4-Fluorobenzyl)-3-{3-[5-(trifluoroacetyl)-2-thienyl]phenyl}acrylamide | 10 | 433 | 434 | 452 | | |
| 127 | 4-[5-(Trifluoroacetyl)-1,3-thiazol-2-yl]pyridinium trifluoroacetate | 8 | 258 | 259 | 277 | | |
| 128 | 1-[2-(4-Acetylphenyl)-1,3-thiazol-5-yl]-2,2,2-trifluoroethanone | 9 | 299 | 300 | 318 | | |
| 129 | 2,2,2-Trifluoro-1-[2-(1-naphthyl)-1,3-thiazol-5-yl]ethanone | 9 | 307 | 308 | 326 | | |
| 130 | 4-[5-(Trifluoroacetyl)-1,3-thiazol-2-yl]benzonitrile | 9 | 282 | 283 | 301 | | |
| 131 | 2,2,2-Trifluoro-1-[2-(4-phenoxyphenyl)-1,3-thiazol-5-yl]ethanone | 9 | 349 | 350 | 368 | | |
| 132 | 1-(2-Biphenyl-4-yl-1,3-thiazol-5-yl)-2,2,2-trifluoroethanone | 9 | 333 | 334 | 352 | | |
| 133 | 2,2,2-Trifluoro-1-{2-[4-(trifluoromethyl)phenyl]-1,3-thiazol-5-yl}ethanone | 9 | 325 | 326 | 344 | | |
| 134 | 2,2,2-Trifluoro-1-[2-(4-nitrophenyl)-1,3-thiazol-5-yl]ethanone | 9 | 302 | 303 | 321 | | |
| 135 | 1-[2-(3,4-Dichlorophenyl)-1,3-thiazol-5-yl]-2,2,2-trifluoroethanone | 9 | 325<br>327<br>329 | 326<br>328<br>330 | 344<br>346<br>348 | | |
| 136 | 1-[2-(4-Bromophenyl)-1,3-thiazol-5-yl]-2,2,2-trifluoroethanone | 8 | 335<br>337 | 336<br>338 | 354<br>356 | | |
| 137 | 1-[2-(3,4-Difluorophenyl)-1,3-thiazol-5-yl]-2,2,2-trifluoroethanone | 9 | 293 | 294 | 312 | | |

EXAMPLE 138

2,2,2-Trifluoro-1-(5-thianthren-1-yl-2-thienyl)ethanone

1H NMR (300 MHz, CD3CN): δ 8.13-8.07 (1H, m), 7.70-7.60 (1H, m), 7.62-7.27 (7H, m).

EXAMPLE 139

1-[5-(2,3-Dihydro-1-benzofuran-5-yl)-2-thienyl]-2,2,2-trifluoroethanone

1H NMR (300 MHz, CD3CN): δ 8.10-7.35 (1H, m), 7.67 (1H, s), 7.59 (1H, d, J=8.3 Hz), 7.48-7.43 (1H, m), 6.84 (1H, d, J=8.3 Hz), 4.63 (2H, t, J=8.8 Hz), 3.26 (2H, t J=8.8 Hz).

EXAMPLE 140 tert-Butyl {4-[5-(trifluoroacetyl)-2-thienyl]phenyl}carbamate $^1$H NMR (300 MHz, CD$_3$CN): δ 8.05-7.97 (1H, m), 7.81-7.66 (3H, m), 7.58-7.77 (3H, m), 1.50 (9H, s).

| Ex | Name | Procedure According To Example | MWt | (M + H)$^+$ | (M + H$_2$O + H) | (M + H$_2$O + Na + H) | (M − H)$^-$ |
|---|---|---|---|---|---|---|---|
| 141 | 2,2,2-Trifluoro-1-(5-phenyl-2-thienyl)ethanone | 3 | 256 | 257 | | | |

The invention claimed is:

1. A compound of formula I:

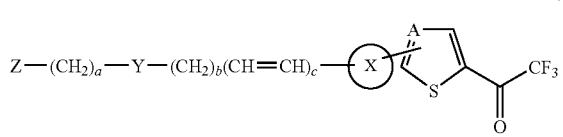

wherein:
a is 0, 1, 2 or 3;
b is 0, 1, 2 or 3;
c is 0, 1 or 2;
A is CH or N;
the X ring is a substituent on a carbon atom of the sulfur containing ring, and is C$_{6-10}$aryl, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms, or a 7-15 membered saturated, partially saturated or unsaturated heterocyclic ring containing 1, 2, 3 or 4 heteroatoms independently selected from N, O and S; optionally substituted by one or more halogen groups;
Y is a direct bond, —O—, >(C=O), >S(O)$_d$, —NR$^2$(C=O)— or —(C=O)NR$^2$—;
d is 0, 1 or 2;
R$^2$ is hydrogen or C$_{1-6}$alkyl;
Z is hydrogen, halogen, cyano, hydroxyl, C$_{1-6}$alkyl, haloC$_{1-6}$alkyl, C$_{1-6}$alkoxy, nitro, N(R$^a$)$_2$; or a ring which is: C$_{3-6}$cycloalkyl; C$_{6-10}$aryl; a 5 or 6 membered saturated or partially saturated heterocyclic ring containing 1, 2 or 3 heteroatoms independently selected from N, O and S; a 5 membered heteroaromatic ring containing 1, 2, 3 or 4 heteroatoms independently selected from N, O and S, not more than one heteroatom of which is O or S; a 6 membered heteroaromatic ring containing 1, 2 or 3 nitrogen atoms; or a 7-10 membered saturated, partially saturated or unsaturated heterocyclic ring containing 1, 2, 3 or 4 heteroatoms independently selected from N, O and S; any of which rings being optionally substituted by one or more groups independently selected from R$^3$;
each R$^a$ is independently hydrogen, C$_{1-6}$alkyl, C$_{1-6}$alkylcarbonyl or SO$_2$R$^b$;
R$^b$ is C$_{1-6}$alkyl, amino, C$_{1-6}$alkylamino or di(C$_{1-6}$alkyl)amino;
each R$^3$ is independently halogen, cyano, oxo, hydroxyl, C$_{1-6}$alkyl, haloC$_{1-6}$alkyl, C$_{1-6}$alkoxy, mercaptoC$_{1-6}$alkyl, haloC$_{1-6}$alkoxy, nitro, N(R$^a$)$_2$, SO$_2$R$^b$, OSO$_2$R$^b$, COR$^c$, C$_{1-6}$alkylSO$_2$R$^b$, R$^d$, C$_{1-6}$alkylR$^d$, C$_{1-6}$alkoxyR$^d$ or C$_{1-6}$alkoxySO$_2$R$^d$;
R$^c$ is hydrogen, C$_{1-6}$alkyl or C$_{1-6}$alkoxy;
R$^d$ is C$_{6-10}$aryl; a 5-membered heteroaromatic ring containing 1, 2, 3 or 4 heteroatoms independently selected from N, O and S, not more than one heteroatom of which is O or S, or a 6 membered heteroaromatic ring containing 1, 2 or 3 nitrogen atoms; any of which rings being optionally substituted by one or more groups independently selected from halogen, C$_{1-6}$alkyl, C$_{1-6}$alkoxy, mercaptoC$_{1-6}$alkyl, haloC$_{1-6}$alkyl, haloC$_{1-6}$alkoxy, amino, C$_{1-6}$alkylamino and di(C$_{1-6}$alkyl)amino;
providing that:
when A is CH and X is phenyl, then (CH=CH)$_c$(CH$_2$)$_b$—Y—(CH$_2$)$_a$—Z is not hydrogen;
or a pharmaceutically acceptable salt or tautomer thereof.

2. The compound of claim 1 of formula II:

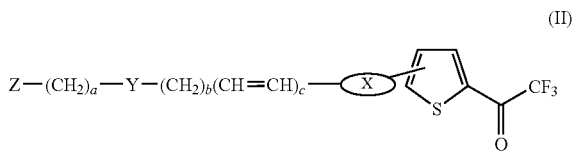

wherein a, b, c, X, Y and Z are as defined in claim 2;
provided that when X is phenyl, then (CH=CH)$_c$(CH$_2$)$_b$—Y—(CH$_2$)$_a$—Z is not hydrogen;
or a pharmaceutically acceptable salt or tautomer thereof.

3. The compound of claim 2 of formula III:

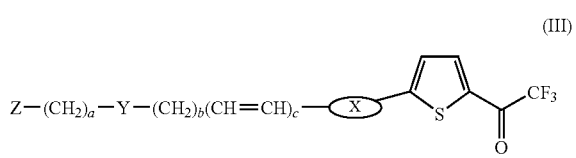

wherein a, b, c, X, Y and Z are as defined in claim 3;
provided that when X is phenyl, then (CH=CH)$_c$(CH$_2$)$_b$—Y—(CH$_2$)$_a$—Z is not hydrogen;
or a pharmaceutically acceptable salt or tautomer thereof.

4. The compound of claim 3 of formula IV:

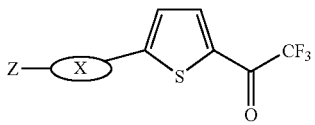

(IV)

wherein X and Z are as defined in claim 4;
provided that when X is phenyl, then Z is not hydrogen;
or a pharmaceutically acceptable salt or tautomer thereof.

5. The compound of claim 1 of formula V:

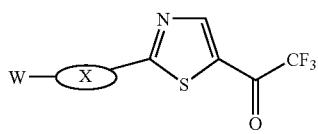

(V)

wherein:

X is $C_{6-10}$aryl, a 5 membered heteroaromatic ring containing 1, 2, 3 or 4 heteroatoms independently selected from N, O and S, not more than one heteroatom of which is O or S, a 6 membered heteroaromatic ring containing 1, 2 or 3 nitrogen atoms, or a 7-15 membered saturated, partially saturated or unsaturated heterocyclic ring containing 1, 2, 3 or 4 heteroatoms independently selected from N, O and S, optionally substituted by one or more halogen groups; and W is hydrogen, halogen, halo$C_{1-6}$alkyl, cyano, nitro, $C_{1-6}$alkoxy, $C_{1-6}$alkylcarbonyl, $C_{6-10}$aryl or $C_{6-10}$aryloxy;

or a pharmaceutically acceptable salt or tautomer thereof.

6. A pharmaceutical composition comprising a compound of claim 1, or a pharmaceutically acceptable salt or tautomer thereof and a pharmaceutically acceptable carrier.

7. The compound of claim 1 that is 3-[5-(Trifluoroacetyl)-2-thienyl]benzoic acid or a pharmaceutically acceptable salt thereof.

8. The compound of claim 1 that is 4-[5-(Trifluoroacetyl)-2-thienyl]benzoic acid or a pharmaceutically acceptable salt thereof.

9. A pharmaceutical composition comprising a compound of claim 7, or a pharmaceutically acceptable salt and a pharmaceutically acceptable carrier.

10. A pharmaceutical composition comprising a compound of claim 8, or a pharmaceutically acceptable salt and a pharmaceutically acceptable carrier.

* * * * *